US010859576B2

(12) United States Patent
Sibson et al.

(10) Patent No.: US 10,859,576 B2
(45) Date of Patent: Dec. 8, 2020

(54) METHOD FOR DIAGNOSING A BRAIN TUMOUR IN A HUMAN

(71) Applicant: Oxford University Innovation Limited, Botley (GB)

(72) Inventors: Nicola R. Sibson, Yarnton (GB); Daniel C. Anthony, Oxford (GB); Alex M. Dickens, Cambridge (GB); James R. Larkin, Headington (GB)

(73) Assignee: Oxford University Innovation Limited, Oxford (GB)

( * ) Notice: Subject to any disclaimer, the term of this patent is extended or adjusted under 35 U.S.C. 154(b) by 200 days.

(21) Appl. No.: 15/578,925

(22) PCT Filed: Jun. 3, 2016

(86) PCT No.: PCT/GB2016/051653
§ 371 (c)(1),
(2) Date: Dec. 1, 2017

(87) PCT Pub. No.: WO2016/193757
PCT Pub. Date: Dec. 8, 2016

(65) Prior Publication Data
US 2018/0172688 A1 Jun. 21, 2018

(30) Foreign Application Priority Data
Jun. 3, 2015 (GB) .................................. 1509658.9

(51) Int. Cl.
*G01N 33/00* (2006.01)
*G01N 33/574* (2006.01)

(52) U.S. Cl.
CPC .............................. *G01N 33/57407* (2013.01)

(58) Field of Classification Search
CPC ............ G01N 33/57407; G01N 33/70; G01N 33/6806
See application file for complete search history.

(56) References Cited

U.S. PATENT DOCUMENTS

| 2004/0224337 A1 | 11/2004 | Foehr et al. |
| 2014/0193920 A1 | 7/2014 | Wong et al. |

FOREIGN PATENT DOCUMENTS

| CN | 103033580 A | 4/2013 |
| WO | 2006/047298 A2 | 5/2006 |
| WO | 2009/087689 A2 | 7/2009 |
| WO | 2013/099827 A1 | 7/2013 |
| WO | 2013/117930 A2 | 8/2013 |
| WO | 2013/163431 A1 | 10/2013 |

OTHER PUBLICATIONS

Petrik, Vladimir et al. "OMICS and brain tumour biomarkers." British Journal of Neurosurgery (2006) 20 275-280. (Year: 2006).*
Wright, Alan J. et al. "Ex-vivo HRMAS of adult brain tumours: metabolite quantification and assignment of tumour biomarkers." Molecular Cancer (2010) 9 66. (Year: 2010).*
An, Y.J., et al., "An NMR Metabolomics Approach for the Diagonosis of Leptomeningeal Carcinomatosis in Lung Adenocarcinoma Cancer Patients," International Journal of Cancer 136(1):162-171, Jan. 2015.
Hattingen, E., et al., "Evaluation of Optimal Echo Time for 1H-Spectroscopic Imaging of Brain Tumors at 3 Tesla," Journal of Magnetic Resonance Imaging 26(2):427-431, Aug. 2007.
Hattingen, E., et al., "Myo-Inositol: A Marker of Reactive Astrogliosis in Glial Tumors?" NMR in Biomedicine 21(3):233-241,Mar. 2008.
Hwang, Y.-F., et al., "Differentiation Among Metastatic Brain Tumors, Radiation Necroses, and Brain Abscesses Using Proton Magnetic Resonance Spectroscopy," Kaohsiung Journal of Medical Sciences 20(9):437-442, Sep. 2004.
Kanno, H., et al., "Transforming Growth Factors in Urine From Patients With Primary Brain Tumors," Journal of Neurosurgery 68:775-780, May 1988.
Kinoshita, Y., et al., "Proton Magnetic Resonance Spectroscopy of Brain Tumors: An In Vitro Study," Neurosurgery 35(4):606-614, Oct. 1994.
Manton, D.J., et al., "Determination of Proton Metabolite Concentrations and Relaxation Parameters in Normal Human Brain and Intracranial Tumours," NMR in Biomedicine 8(3):104-112, May 1995.
Rezvanizadeh, A., et al., "The Effects of Voxel Localization and Time of Echo on the Diagnostic Accuracy of Cystic Brain Tumors in 3 Tesla Magnetic Resonance Spectroscopy," Iranian Journal of Radiology 9(4):195-201, Nov. 2012.
Smith, E.R., et al., "Urinary Biomarkers Predict Brain Tumor Presence and Response to Therapy," Clinical Cancer Research 14(8):2378-2386, Apr. 2008.
Ueda, T., et al., "Clinical Value of the Sequential Study of the Uric Acid in CSF in Patients With Cerebral Diseases: Part 1. Brain Tumor and the Effect of Irradiation," No to Shinkei = Brain and Nerve 36(3):255-260, Mar. 1984.

(Continued)

*Primary Examiner* — Christopher Adam Hixson
(74) *Attorney, Agent, or Firm* — Christensen O'Connor Johnson Kindness PLLC

(57) ABSTRACT

An in vitro method for diagnosing a brain tumour in a human test subject comprising: determining the concentration of at least two metabolites comprised in a biofluid sample obtained from the human test subject; comparing the concentration of the at least two metabolites in the biofluid sample with the concentration of the same at least two metabolites in at least one reference standard obtained from a non-tumour bearing subject and/or a tumour bearing subject; and identifying a concentration difference for each of the at least two metabolites in the biofluid sample relative to the reference standard; wherein the concentration difference for each of the at least two metabolites in the biofluid sample correlates with the presence of a brain tumour. The invention also relates to a data-storage medium comprising data obtained by a method of the invention.

11 Claims, 8 Drawing Sheets

(56) References Cited

OTHER PUBLICATIONS

Wilson, M., et al., "High Resolution Magic Angle Spinning 1H NMR of Childhood Brain and Nervous System Tumours," Molecular Cancer 8(6):11 pages, Feb. 2009.
Search Report dated Feb. 29, 2016, issued in Application No. GB 1509658.9, filed Jun. 3, 2015, 6 pages.
International Search Report and Written Opinion dated Sep. 8, 2016, issued in International Application No. PCT/GB2016/051653, filed Jun. 3, 2016, 13 pages.
International Preliminary Report on Patentability dated Dec. 6, 2017, issued in International Application No. PCT/GB2016/051653, filed Jun. 3, 2016, 8 pages.

\* cited by examiner

A

B

| True membership | Predicted membership | |
| --- | --- | --- |
| | Control | Day 5 |
| Control | 13 | 4 |
| Day 5 | 2 | 7 |

C

| True membership | Predicted membership | |
| --- | --- | --- |
| | Control | Day 10 |
| Control | 12 | 4 |
| Day 10 | 2 | 7 |

D

| True membership | Predicted membership | |
| --- | --- | --- |
| | Control | Day 21 |
| Control | 16 | 0 |
| Day 21 | 1 | 8 |

E

| True membership | Predicted membership | |
| --- | --- | --- |
| | Control | Day 35 |
| Control | 16 | 0 |
| Day 35 | 0 | 9 |

METHOD FOR DIAGNOSING A BRAIN TUMOUR IN A HUMAN

FIELD OF THE INVENTION

The present invention relates to an in vitro method for diagnosing a brain tumour in a human test subject as well as a data-storage medium comprising data obtained by a method of the invention.

BACKGROUND

Metastasis, the spread of a tumour from its primary site to a distant location, is a leading cause of cancer mortality and remains a significant hurdle. Approximately 20-40% of cancer patients will develop brain metastases. Lung cancer, breast cancer and melanoma are the most common primary tumours in patients with brain metastasis and between them they account for 67 to 80% of all cases. Critically, brain metastases present a particularly tough clinical challenge owing to the nature of the blood-brain barrier (BBB) which thwarts attempts to diagnose tumours and also inhibits their treatment with most systemically active therapeutic agents.

Brain metastases are diagnosed by imaging methods, for which the current clinical gold standard is gadolinium-enhanced MRI. However prognosis is poor, which is largely thought to reflect the late stage of diagnosis. The late diagnosis is a direct consequence of the fact that gadolinium-MRI is only sensitive to tumours large enough for the BBB to be compromised.

Spectroscopic analysis of biological fluids (biofluids), using high resolution $^1$H NMR, has become increasingly common in drug safety assessment as a method for identifying target organ toxicity. This approach involves the acquisition of a $^1$H NMR spectrum from biofluid samples, e.g. urine or serum, followed by analysis of these data using a multivariate statistical pattern recognition technique. This approach is powerful because it requires no a priori knowledge, but rather identifies metabolites solely based on their correlated variation between treatment groups. Thus these techniques, such as orthogonal partial least squares discriminant analysis (OPLS-DA), are able to identify distinct patterns of metabolites whose variation as a whole is characteristic of the disease, rather than requiring identification of a single unique biomarker.

Using this biofluid metabolomics approach, it has been previously shown that it is possible to distinguish between groups of animals with either a predominantly macrophage-mediated or a neutrophil-rich lesion in the brain. This finding indicated that the approach is sensitive not only to the presence of disease in the brain, but to the pathological profile of that disease. More recently, it has been shown that this technique can be used to differentiate between groups of patients with multiple sclerosis (WO2013/117930 the teaching of which is incorporated herein by reference).

There is therefore a need for more sensitive methods for diagnosing a brain tumour. There is a need for more effective methods for diagnosing a brain tumour. There is a need for improved methods for differentiating between tumour type and/or stage.

SUMMARY OF THE INVENTION

The present invention meets one or more of the above needs by providing an in vitro method for diagnosing a brain tumour in a human test subject comprising:

a. Determining the concentration of at least two metabolites comprised in a biofluid sample obtained from the human test subject;
b. Comparing the concentration of the at least two metabolites in the biofluid sample with the concentration of the same at least two metabolites in at least one reference standard obtained from a non-tumour bearing subject and/or a tumour bearing subject; and
c. Identifying a concentration difference for each of the at least two metabolites in the biofluid sample relative to the reference standard;

wherein the concentration difference for each of the at least two metabolites in the biofluid sample correlates with the presence of a brain tumour.

The present invention further provides an in vitro method for differentiating between a primary and a secondary brain tumour in a human test subject comprising:

a. Determining the concentration of at least two metabolites comprised in a biofluid sample obtained from the human test subject;
b. Comparing the concentration of the at least two metabolites in the biofluid sample with the concentration of the same at least two metabolites in at least one reference standard obtained from a subject having a primary brain tumour and/or a subject having a secondary brain tumour; and
c. Identifying a concentration difference for each of the at least two metabolites in the biofluid sample relative to the reference standard;

wherein the concentration difference for each of the at least two metabolites in the biofluid sample allows differentiation between a primary and a secondary brain tumour.

The invention also provides a data-storage medium comprising data obtained by a method of the invention.

The present invention also provides an in vitro method for diagnosing a brain tumour in a human test subject comprising:

a. obtaining a data set showing data for at least two metabolites comprised in a biofluid sample obtained from the human test subject using a method selected from nuclear magnetic resonance (NMR) spectroscopy, mass spectrometry, HPLC-UV and infrared spectrometry (preferably NMR spectroscopy);
b. Comparing the data set showing data for the at least two metabolites for the biofluid sample with a data set for the same at least two metabolites in at least one reference standard obtained from a non-tumour bearing subject and/or a tumour bearing subject; and
c. Identifying a difference in the data set obtained for each of the at least two metabolites in the biofluid sample relative to the reference standard;

wherein the difference in the data set for each of the at least two metabolites in the biofluid sample correlates with the presence of a brain tumour.

Suitably, the data set may be a trace obtainable from a spectroscopic method, suitably a trace obtainable from NMR spectroscopy.

Advantages

The methods of the present invention achieve a number of advantages. The present invention provides an effective and/or reliable method for diagnosing the presence of a brain tumour in a human test subject. Moreover, the methods of the invention allow for the distinction between primary and/or secondary brain tumours and/or systemic metastases and/or allow the stage of the tumour to be determined.

Additionally, by comparing and identifying differences in the concentration of at least two metabolites comprised in a sample from a human test subject and at least one reference standard early diagnosis of a brain tumour can be achieved. Dependent on the reference standard used and the differences in metabolite concentrations determined, the early diagnosis of a primary brain tumour, secondary brain tumour (e.g. a micrometastatic secondary brain tumour) can be achieved.

The present invention therefore provides new and sensitive methods for earlier detection of brain metastases. Earlier detection of brain metastases means that treatments could be better directed and prognosis improved, whilst harmful and unnecessary treatment of at-risk cancer patients that do not have brain metastases could be avoided.

The methods of the invention comprise obtaining a sample from a human test subject. The present invention allows the concentration of at least two metabolites to be determined with only minimal processing of the sample obtained from the human test subject. Advantageously, the present invention allows for a simple and/or non-invasive (e.g. not requiring any surgery or biopsy) and/or quick and/or inexpensive and/or safe processing of a sample from a human test subject.

Furthermore, the minimal processing of the sample helps prevent the introduction of false positives and/or the provision of false negatives, especially when compared to other methods which may require purification of a metabolite, for example.

Additional advantages arising from the use of the present invention (e.g. due to the minimal processing of samples) is that it does not require a highly trained individual to obtain the sample from the human test subject and/or does not require significant training of the operator.

DETAILED DESCRIPTION

A seminal finding of the present invention is that a brain tumour in a test subject can be diagnosed and/or a primary and a secondary brain tumour in a human test subject can be differentiated between by carrying out the methods described herein.

The data presented herein relate to use of a mouse as cancer cell host, however the model employed is believed to have high predictive accuracy for diagnosis of human brain tumours and/or differentiation between human brain tumour types. Metabolite concentration data obtained and presented herein for metastatic human breast carcinoma cells (MDA-231-BR-GFP) (see Example 2) was similar to that obtained using mouse tumour cells, thus validating the present model for human diagnostic purposes.

Therefore the invention provides an in vitro method for diagnosing a brain tumour in a human test subject comprising:
  a. Determining the concentration of at least two metabolites comprised in a biofluid sample obtained from the human test subject;
  b. Comparing the concentration of the at least two metabolites in the biofluid sample with the concentration of the same at least two metabolites in at least one reference standard obtained from a non-tumour bearing subject and/or a tumour bearing subject; and
  c. Identifying a concentration difference for each of the at least two metabolites in the biofluid sample relative to the reference standard;

wherein the concentration difference for each of the at least two metabolites in the sample correlates with the presence of a brain tumour.

The invention provides an in vitro method for differentiating between a primary and a secondary brain tumour in a human test subject comprising:
  a. Determining the concentration of at least two metabolites comprised in a biofluid sample obtained from the human test subject;
  b. Comparing the concentration of the at least two metabolites in the biofluid sample with the concentration of the same at least two metabolites in at least one reference standard obtained from a subject having a primary brain tumour and/or a subject having a secondary brain tumour; and
  c. Identifying a concentration difference for each of the at least two metabolites in the biofluid sample relative to the reference standard;

wherein the concentration difference for each of the at least two metabolites in the biofluid sample allows differentiation between a primary and a secondary brain tumour.

The term "brain tumour" as used herein refers to an abnormal growth of tissue present in the brain and encompasses both malignant tumours as well as benign tumours. Suitably, the brain tumour may be a malignant tumour. Brain tumours in accordance with the invention may be primary brain tumours or secondary brain tumours.

The term "primary brain tumour" as used herein refers to a brain tumour that originated in the brain. In other words a "primary brain tumour" is a tumour that has developed in situ in the brain where tumour progression began and proceeded to yield a cancerous mass. Suitably, a primary brain tumour may be comprised of cells that form up the tissue of, or surrounding, the brain. A primary brain tumour differs from a secondary brain tumour which has not originated in the brain.

The method according to the invention may diagnose (or may be for diagnosing) a primary brain tumour.

The term "secondary brain tumour" as used herein refers to a tumour in the brain that did not originate in the brain. In other words a "secondary brain tumour" is a tumour that derives from a tumour that has developed ex situ to the brain in another tissue of the body and from which one or more cells have been transported to the brain, at which site they then form a secondary brain tumour. One or more tumour cells from which a secondary brain tumour forms may be transported to the brain by any known means. Suitably by the process of metastasis.

The method according to the invention may diagnose (or may be for diagnosing) a secondary brain tumour.

Suitably, the secondary brain tumour may be at a micrometastatic stage.

The term "micrometastatic stage" as used herein means that a secondary tumour (e.g. a secondary brain tumour) which has metastasised from another tissue of the body is too miniscule to be detected by conventional techniques. For example, a micrometastatic tumour may be a tumour that is too miniscule to be visualised using an imaging technique known in the art.

The term "test subject" as used herein refers to a subject that is the subject of the brain tumour diagnosis and/or method for differentiating between a primary and a secondary brain tumour. The term "test subject" as used herein refers to a human test subject.

The concentration of at least two metabolites comprised in a sample obtained from a test subject may be determined by any suitable method known to one skilled in the art. The concentration of the at least two metabolites may be determined by one or more method selected from the group consisting of nuclear magnetic resonance (NMR) spectroscopy, mass spectrometry, HPLC-UV, infrared spectrometry and a biochemical assay.

The biochemical assay may be an enzymatic assay. Suitably such an assay may be useful when detecting the concentration of the metabolite uric acid and/or allantoin.

One suitable enzymatic assay for determining the presence of the metabolite uric acid may be the Amplex® Red Uric Acid/Uricase Assay Kit (commercially available from Life Technologies Ltd. Product code A22181 (https://www.lifetechnologies.com/order/catalog/product/A22181)).

Suitably, the concentration of the at least two metabolites may be determined using NMR spectroscopy, more suitably, H-NMR spectroscopy.

The "at least two metabolites" may be any two or more metabolites identified that differ between a sample obtained from a test subject and a sample obtained from a non-tumour bearing subject, a tumour bearing subject, a subject having a primary brain tumour, a subject having a secondary brain tumour or combinations thereof.

One or more of the at least two metabolites may be selected from the group consisting of: uric acid, allantoin, citrate, trimethylamine (TMA), trimethylamine-N-oxide (TMAO), 2-oxoglutarate, creatinine, taurine, creatine and phosphocreatine.

One or more of the at least two metabolites may be selected from citrate and/or 2-oxoglutarate.

One or more of the at least two metabolites may be selected from creatinine, uric acid and/or allantoin.

One or more of the at least two metabolites may be selected from TMAO, TMA, creatine, phosphocreatine, taurine or combinations thereof.

In a particularly preferred embodiment, the at least two metabolites for use in a method of the present invention may comprise (or consist of) one or more of creatinine, creatine and/or phosphocreatine (suitably wherein the at least one reference standard is a reference standard from a non-tumour bearing subject).

At least two metabolites for use in the method of the invention may be selected from the group consisting of: uric acid, allantoin, citrate, trimethylamine (TMA), trimethylamine-N-oxide (TMAO), 2-oxoglutarate, creatinine, taurine, creatine and phosphocreatine.

In another embodiment at least two metabolites for use in the method of the invention may be selected from the group consisting of: allantoin, citrate, trimethylamine (TMA), trimethylamine-N-oxide (TMAO), 2-oxoglutarate, creatinine, taurine, creatine and phosphocreatine.

In a further embodiment at least two metabolites for use in the method of the invention may be selected from the group consisting of: allantoin, citrate, trimethylamine (TMA), trimethylamine-N-oxide (TMAO), 2-oxoglutarate, creatinine, taurine, creatine and phosphocreatine, a metabolite having an unidentified triplet centred at $\delta=2.38$, and an unidentified doublet centred at $\delta=3.11$.

At least three metabolites for use in the method of the invention may be selected from the group consisting of: uric acid, allantoin, citrate, trimethylamine (TMA), trimethylamine-N-oxide (TMAO), 2-oxoglutarate, creatinine, taurine, creatine and phosphocreatine.

In another embodiment at least three metabolites for use in the method of the invention may be selected from the group consisting of: uric acid, citrate, trimethylamine (TMA), trimethylamine-N-oxide (TMAO), 2-oxoglutarate, creatinine, taurine, creatine and phosphocreatine.

At least four metabolites for use in the method of the invention may be selected from the group consisting of: uric acid, allantoin, citrate, trimethylamine (TMA), trimethylamine-N-oxide (TMAO), 2-oxoglutarate, creatinine, taurine, creatine and phosphocreatine.

In another embodiment at least four metabolites for use in the method of the invention may be selected from the group consisting of: uric acid, citrate, trimethylamine (TMA), trimethylamine-N-oxide (TMAO), 2-oxoglutarate, creatinine, taurine, creatine and phosphocreatine.

At least five metabolites for use in the method of the invention may be selected from the group consisting of: uric acid, allantoin, citrate, trimethylamine (TMA), trimethylamine-N-oxide (TMAO), 2-oxoglutarate, creatinine, taurine, creatine and phosphocreatine.

In another embodiment at least five metabolites for use in the method of the invention may be selected from the group consisting of: uric acid, citrate, trimethylamine (TMA), trimethylamine-N-oxide (TMAO), 2-oxoglutarate, creatinine, taurine, creatine and phosphocreatine.

At least six metabolites for use in the method of the invention may be selected from the group consisting of: uric acid, allantoin, citrate, trimethylamine (TMA), trimethylamine-N-oxide (TMAO), 2-oxoglutarate, creatinine, taurine, creatine and phosphocreatine.

In another embodiment at least six metabolites for use in the method of the invention may be selected from the group consisting of: uric acid, citrate, trimethylamine (TMA), trimethylamine-N-oxide (TMAO), 2-oxoglutarate, creatinine, taurine, creatine and phosphocreatine.

At least seven metabolites for use in the method of the invention may be selected from the group consisting of: uric acid, allantoin, citrate, trimethylamine (TMA), trimethylamine-N-oxide (TMAO), 2-oxoglutarate, creatinine, taurine, creatine and phosphocreatine.

In another embodiment at least seven metabolites for use in the method of the invention may be selected from the group consisting of: uric acid, citrate, trimethylamine (TMA), trimethylamine-N-oxide (TMAO), 2-oxoglutarate, creatinine, taurine, creatine and phosphocreatine.

At least eight metabolites for use in the method of the invention may be selected from the group consisting of: uric acid, allantoin, citrate, trimethylamine (TMA), trimethylamine-N-oxide (TMAO), 2-oxoglutarate, creatinine, taurine, creatine and phosphocreatine.

In another embodiment at least eight metabolites for use in the method of the invention may be selected from the group consisting of: uric acid, citrate, trimethylamine (TMA), trimethylamine-N-oxide (TMAO), 2-oxoglutarate, creatinine, taurine, creatine and phosphocreatine.

At least nine metabolites for use in the method of the invention may be selected from the group consisting of: uric acid, allantoin, citrate, trimethylamine (TMA), trimethylamine-N-oxide (TMAO), 2-oxoglutarate, creatinine, taurine, creatine and phosphocreatine.

In another embodiment at least nine metabolites for use in the method of the invention may be selected from the group consisting of: uric acid, citrate, trimethylamine (TMA), trimethylamine-N-oxide (TMAO), 2-oxoglutarate, creatinine, taurine, creatine and phosphocreatine.

At least ten metabolites for use in the method of the invention may be selected from the group consisting of: uric acid, allantoin, citrate, trimethylamine (TMA), trimethylamine-N-oxide (TMAO), 2-oxoglutarate, creatinine, taurine, creatine and phosphocreatine.

In another embodiment at least ten metabolites for use in the method of the invention may be selected from the group consisting of: uric acid, citrate, trimethylamine (TMA), trimethylamine-N-oxide (TMAO), 2-oxoglutarate, creatinine, taurine, creatine and phosphocreatine.

The metabolite may be one or more selected from the following Table (Table A):

| Trivial name | IUPAC systematic name from chemspider | NMR identification (HMDB) | Complete range of possible buckets which include portions of a metabolite peak (ppm) |
|---|---|---|---|
| Allantoin | 1-(2,5-Dioxo-4-imidazolidinyl)urea | Singlet at 5.38 ppm | 5.37-5.38, 5.38-5.39, 5.39-5.40 |
| Citrate | 2-hydroxypropane-1,2,3-tricarboxylate | Doublet at 2.67 ppm and 2.64 ppm; doublet at 2.54 ppm and 2.51 ppm | 2.52-2.53, 2.53-2.54, 2.54-2.55, 2.55-2.56, 2.66-2.67, 2.67-2.68, 2.68-2.69, 2.69-2.70 |
| Trimethylamine | N,N-Dimethylmethanamine | Singlet at 2.89 ppm | 2.88-2.89, 2.89-2.90 |
| Trimethylamine-N-oxide | Trimethylamine oxide | Singlet at 3.25 ppm | 3.26-3.27, 3.27-3.28 |
| 2-oxoglutarate | 2-Oxopentanedioate | Triplet at 3.01, 3.00 and 2.98 ppm; triplet at 2.44, 2.43 and 2.42 ppm | 2.41-2.42, 2.42-2.43, 2.43-2.44, 2.44-2.45, 2.97-2.98, 2.98-2.99, 2.99-3.00, 3.00-3.01, 3.01-3.02 |
| Creatinine | 2-Imino-1-methyl-2,5-dihydro-1H-imidazol-4-ol | Singlet at 4.05 ppm; larger singlet at 3.03 ppm | 3.03-3.04, 3.04-3.05, 4.06-4.07 |
| Taurine | 2-Aminoethanesulfonic acid | Triplet at 3.43, 3.42 and 3.40 ppm; larger triplet at 3.26, 3.25 and 3.24 ppm | 3.23-3.24, 3.24-3.25, 3.25-3.26, 3.26-3.27, 3.39-3.40, 3.40-3.41, 3.41-3.42, 3.42-3.43, 3.43-3.44 |
| Creatine | N-Carbamimidoyl-N-methylglycine | Singlet at 3.92 ppm and larger singlet at 3.02 ppm | 3.01-3.02, 3.02-3.03, 3.91-3.92, 3.92-3.93 |
| Phosphocreatine* | N-Methyl-N-(N-phosphonocarbamimidoyl)glycine | Singlet at 3.93 ppm and larger singlet at 3.03 ppm | 3.02-3.03, 3.03-3.04, 3.92-3.93, 3.93-3.94 |

*The closeness between creatine and phosphocreatine explains why they are indistinguishable here.

The data indicated above are published spectra are from the Human Metabolome Database (hmdb.ca) at pH 7.0 the contents of which is incorporated herein in its entirety by reference.

The skilled person will understand that owing to the particular method used there may be subtle shifts in the values obtained using NMR. Therefore in some instances the values provided for a metabolite may vary.

In one embodiment a metabolite for use in the present invention may be any one (suitably two or more) of the metabolites indicated in Table A above. Suitably, the metabolite may have an NMR (e.g. $^1$H-NMR) profile having one or more of the buckets indicated in Table A.

In one embodiment the metabolite may be any one of the metabolites indicated in the table above other than allantoin.

The term "uric acid" as used herein is synonymous with 7,9-Dihydro-1H-purine-2,6,8(3H)-trione and refers to a chemical compound with formula $C_5H_4N_4O_3$.

The term "allantoin" as used herein is synonymous with 1-(2,5-Dioxo-4-imidazolidinyl) urea and refers to a chemical compound with formula $C_4H_6N_4O_3$. The terms "5-ureidohydantoin" or "glyoxyldiureide" may also be used synonymously. Suitably allantoin may have a $^1$H-NMR profile of a singlet at 5.38 ppm. Suitably, allantoin may have a $^1$H-NMR profile of ($\delta$=5.38-5.39).

In one embodiment allantoin may have a $^1$H-NMR profile comprising (or consisting of) one or more (suitably all) of the following: $\delta$=5.37-5.38, $\delta$=5.38-5.39 and/or $\delta$=5.39-5.40.

The term "citrate" as used herein is synonymous with 2-hydroxypropane-1,2,3-tricarboxylate and refers to a chemical compound having the formula $C_6H_5O_7^{3-}$. Suitably citrate may have a $^1$H-NMR profile of a doublet at 2.67 ppm and 2.64 ppm; doublet at 2.54 ppm and 2.51 ppm. Suitably, citrate may have a $^1$H-NMR profile of ($\delta$=2.52-2.53).

In one embodiment citrate may have a $^1$H-NMR profile comprising (or consisting of) one or more (suitably all) of the following: $\delta$=2.52-2.53, $\delta$=2.53-2.54, $\delta$=2.54-2.55, $\delta$=2.55-2.56, $\delta$=2.66-2.67, $\delta$=2.67-2.68, $\delta$=2.68-2.69 and/or $\delta$=2.69-2.70.

The term "trimethylamine" is used herein synonymously with "TMA" and refers to a chemical compound with the formula $N(CH_3)_3$. Suitably trimethylamine may have a singlet at 2.89 ppm. Suitably, trimethylamine may have a $^1$H-NMR profile of ($\delta$=2.89-2.90).

In one embodiment TMA may have a $^1$H-NMR profile comprising (or consisting of) one or more (suitably all) of the following: $\delta$=2.88-2.89 and/or $\delta$=2.89-2.90.

The term "trimethylamine-N-oxide" is used herein synonymously with "TMAO" and refers to a chemical compound with the formula $(CH_3)_3NO$. Suitably TMAO may have a singlet at 3.25 ppm. Suitably, trimethylamine-N-oxide may have a $^1$H-NMR profile of ($\delta$=3.27-3.28).

In one embodiment TMAO may have a $^1$H-NMR profile comprising (or consisting of) one or more (suitably all) of the following: δ=3.26-3.27 and/or δ=3.27-3.28.

The term "2-oxoglutarate" is synonymous with "α-ketoglutarate" and 2-Oxopentanedioic acid and has the formula $C_5H_6O_5$. Suitably 2-oxoglutarate may have a triplet at 3.01, 3.00 and 2.98 ppm; triplet at 2.44, 2.43 and 2.42 ppm. Suitably, 2-oxoglutarate may have a $^1$H-NMR profile of (δ=2.43-2.45).

In one embodiment 2-oxoglutarate may have a $^1$H-NMR profile comprising (or consisting of) one or more (suitably all) of the following: δ=2.41-2.42, δ=2.42-2.43, δ=2.43-2.44, δ=2.44-2.45, δ=2.97-2.98, δ=2.98-2.99, δ=2.99-3.00, δ=3.00-3.01 and/or δ=3.01-3.02.

The term "creatinine" as used herein is synonymous with 2-Amino-1-methyl-5H-imidazol-4-one and/or 2-Amino-1-methyl-1H-imidazol-4-ol and refers to a compound having the formula $C_4H_7N_3O$. Suitably creatinine may have a singlet at 4.05 ppm; larger singlet at 3.03 ppm. Suitably creatinine may have a $^1$H-NMR profile of (δ=4.06-4.07 and/or δ=3.03-3.04). Without wishing to be bound by theory it is believed that creatinine is a breakdown product of creatine phosphate in muscle and/or brain.

In one embodiment creatinine may have a $^1$H-NMR profile comprising (or consisting of) one or more (suitably all) of the following: δ=3.03-3.04, δ=3.04-3.05 and/or δ=4.06-4.07.

The term "taurine" (synonymous with "2-aminoethanesulfonic acid") refers to a chemical compound having the formula $C_2H_7NO_3S$. Suitably taurine may have a triplet at 3.43, 3.42 and 3.40 ppm; larger triplet at 3.26, 3.25 and 3.24 ppm. Suitably taurine may have a $^1$H-NMR profile of (δ=3.27-3.44).

In one embodiment taurine may have a $^1$H-NMR profile comprising (or consisting of) one or more (suitably all) of the following: δ=3.23-3.24, δ=3.24-3.25, δ=3.25-3.26, δ=3.26-3.27, δ=3.39-3.40, δ=3.40-3.41, δ=3.41-3.42, δ=3.42-3.43 and/or δ=3.43-3.44.

The term "creatine" as used herein is synonymous with 2-[Carbamimidoyl(methyl)amino]acetic acid and refers to a chemical compound having the formula $C_4H_9N_3O_2$. Suitably creatine may have a singlet at 3.92 ppm and larger singlet at 3.02 ppm. Suitably creatine may have a $^1$H-NMR profile of (δ=3.93-3.94).

In one embodiment creatine may have a $^1$H-NMR profile comprising (or consisting of) one or more (suitably all) of the following: δ=3.01-3.02, δ=3.02-3.03, δ=3.91-3.92 and/or δ=3.92-3.93.

The term "phosphocreatine" as used herein is synonymous with N-Methyl-N-(phosphonocarbamimidoyl)glycine and refers to a chemical compound having the formula $C_4H_{10}N_3O_5P$. Suitably phosphocreatine may have a singlet at 3.93 ppm and larger singlet at 3.03 ppm. Suitably phosphocreatine may have a $^1$H-NMR profile of (δ=3.93-3.94).

In one embodiment phosphocreatine may have a $^1$H-NMR profile comprising (or consisting of) one or more (suitably all) of the following: δ=3.02-3.03, δ=3.03-3.04, δ=3.92-3.93, δ=3.93-3.94.

The $^1$H-NMR profile values referred to for the metabolites above may be obtained using any technique known in the art. Suitably one or more of the data acquisition and/or analysis techniques discussed below may be used.

The $^1$H-NMR spectroscopy may be carried out by any method known in the art. The skilled person will be aware that performing $^1$H-NMR spectroscopy under different conditions may provide different $^1$H-NMR spectroscopy data for the metabolites.

The values provided herein may be determinable by the following procedure, however the method of the invention is not limited to performing $^1$H-NMR spectroscopy in accordance with the following:

a) Samples are defrosted on ice and 50 μL from each are placed in a 5 mm NMR tube and diluted to a final volume of 600 μL with phosphate buffer (0.24M sodium phosphate, pH 7.4, 0.1% sodium azide, 0.8% sodium chloride) in $D_2O$ containing 1 mM TSP (3-trimethylsilyl-1-[2,2,3,3,-$^2H_4$] propionate) as an internal standard;
b) $^1$H NMR spectra are acquired for each sample at 700 MHz (Bruker Avance III spectrometer equipped with a $^1$H TCI cryoprobe, Bruker, Coventry, UK);
c) For all samples a 1D NOESY pre-saturation sequence, with solvent pre-saturation during the relaxation delay (2 s) and mixing time (10 ms) is used;
d) Two dimensional $^1$H NMR spectra is acquired from a single sample within each group to assist with metabolite identification;
e) The 2D correlation spectroscopy (COSY) spectra are acquired on the same spectrometer as the 1D NMR spectra;
f) The COSY spectra are acquired with 1.5 s solvent presaturation, a spectral width of 10 ppm (7002 Hz), and 16 or 32 transients pert, increment for 256 increments;
g) All NMR experiments are conducted at 293K;
h) The 1D $^1$H plasma spectra are imported into Matlab (MathWorks, Nantick, USA) using an RBNMR script (the RBNMR script is an open-source script published at Matlab Central which reads raw spectrometer data and imports into a Matlab-compatible form. It is published under the BSD licence and can be found at: http://uk.mathworks.com/matlabcentral/fileexchange/40332-rbnmr) then automatically phased using a method optimised for signal-dense spectra (Bao et al. 2013);
i) Spectra with gross distortions or phasing anomalies are excluded at this stage;
j) Spectra are baseline corrected using a $3^{rd}$ order polynomial fitted to regions without peaks (Beek 2007) then aligned to the TSP peak at 0 ppm;
k) (Optional step when the biofluid sample is a urine sample) Spectra are unit-scaled to the summed spectrum integral, excluding the water and TSP peak regions;
l) Coarsely aligned spectra re then refined by non-linear warping to account for subtle peak shifts arising from differing sample pH, ionic strength etc. (Skov et al. 2006);
m) Aligned spectra are sub-divided into 0.01 ppm regions (δ=start of integral region) from 0.2 to 9.6 ppm and integrated to yield 940 independent variables for each sample; and
n) The regions covering the variable water peak (4.7 to 5.0 ppm) and urea peak (5.70 to 5.95 ppm) are excluded along with the region covering a contaminant methanol peak (3.35 to 3.38 ppm).

Major $^1$H-NMR profile peaks for metabolites for use in the present invention are detailed in the following embodiments (and throughout), however said metabolites may also have one or more (suitably all) of the $^1$H-NMR profile peaks indicated for said metabolite in Table A.

Therefore the two or more metabolites may have a $^1$H-NMR profile selected from the group consisting of: δ=5.38-5.39, δ=2.52-2.53, δ=2.89-2.90, δ=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11. Preferably the $^1$H-NMR profiles detailed and used herein may be obtained using the preferred data acquisition and analysis methods above.

One or more of the at least two metabolites may be selected from $\delta$=2.52-2.53 and/or $\delta$=2.43-2.45.

One or more of the at least two metabolites may be selected from $\delta$=4.06-4.07 and/or $\delta$=3.03-3.04 and/or $\delta$=5.38-5.39.

One or more of the at least two metabolites may be selected from $\delta$=3.27-3.28, $\delta$=2.89-2.90, $\delta$=3.93-3.94, $\delta$=3.27-3.44 or combinations thereof.

At least two metabolites for use in the method of the invention may be selected from the group consisting of: $\delta$=5.38-5.39, $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

In another embodiment at least two metabolites for use in the method of the invention may be selected from the group consisting of: $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

At least three metabolites for use in the method of the invention may be selected from the group consisting of: $\delta$=5.38-5.39, $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

In another embodiment at least three metabolites for use in the method of the invention may be selected from the group consisting of: $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

At least four metabolites for use in the method of the invention may be selected from the group consisting of: $\delta$=5.38-5.39, $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

In another embodiment at least four metabolites for use in the method of the invention may be selected from the group consisting of: $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

At least five metabolites for use in the method of the invention may be selected from the group consisting of: $\delta$=5.38-5.39, $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

In another embodiment at least five metabolites for use in the method of the invention may be selected from the group consisting of: $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

At least six metabolites for use in the method of the invention may be selected from the group consisting of: $\delta$=5.38-5.39, $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

In another embodiment at least six metabolites for use in the method of the invention may be selected from the group consisting of: $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

At least seven metabolites for use in the method of the invention may be selected from the group consisting of: $\delta$=5.38-5.39, $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

In another embodiment at least seven metabolites for use in the method of the invention may be selected from the group consisting of: $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

At least eight metabolites for use in the method of the invention may be selected from the group consisting of: $\delta$=5.38-5.39, $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

In another embodiment at least eight metabolites for use in the method of the invention may be selected from the group consisting of: $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

At least nine metabolites for use in the method of the invention may be selected from the group consisting of: $\delta$=5.38-5.39, $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

In another embodiment at least nine metabolites for use in the method of the invention may be selected from the group consisting of: $\delta$=2.52-2.53, $\delta$=2.89-2.90, $\delta$=3.27-3.28, $\delta$=2.43-2.45, $\delta$=4.06-4.07 and/or $\delta$=3.03-3.04, $\delta$=3.27-3.44, $\delta$=3.93-3.94, $\delta$=2.38 and $\delta$=3.11.

The sample obtained from a human test subject or at least one standard obtained from a non-tumour bearing subject, a tumour bearing subject, a subject having a primary brain tumour, a subject having a secondary brain tumour or combinations thereof may suitably be a biological fluid (biofluid) sample or a fraction thereof. The biofluid sample may be obtained using any suitable techniques known to the skilled person including inter alia venepuncture, lumbar puncture (synonymous with spinal tap), catheter extraction and/or urination.

The biofluid sample may be a urine sample, a blood sample, a cerebrospinal fluid sample, a lymph sample, combinations thereof or a fraction thereof.

In a particularly preferred embodiment the biofluid sample may be a urine sample.

Suitably the biofluid sample may be a blood sample.

The term "blood" as used herein comprises whole blood, blood serum (henceforth "serum") and blood plasma (henceforth "plasma"). Serum and plasma are derived from blood and thus may be considered as specific subtypes within the broader genus "blood". Processes for obtaining serum or plasma from blood are known in the art. For example, it is known in the art that blood can be subjected to centrifugation in order to separate red blood cells, white blood cells, and plasma. Serum is defined as plasma that lacks clotting factors. Serum can be obtained by centrifugation of blood in which the clotting process has been triggered. Optionally, this can be carried out using specialised centrifuge tubes designed for this purpose.

The biofluid sample for use in the present invention may not have undergone any processing or may have only undergone minimal processing after being obtained from a human test subject.

The term "fraction thereof" when used herein in the context of biofluid fractions refers to a portion of a biofluid fraction obtainable or obtained following processing of a biofluid. Suitably a biofluid fraction refers to one or more constituent(s) of a biofluid that has been separated from one or more further biofluid constituent(s). For example, a fraction of a blood sample may be blood plasma fraction.

The methods of the present invention are in vitro methods. Thus, they can be carried out in vitro on an isolated sample that has been obtained from a test subject.

In the methods of the invention the concentration of at least two metabolites comprised in a sample obtained from a human test subject is compared with the concentration of the same at least two metabolites in at least one reference standard. Such a comparison may therefore give rise to a relative concentration of the at least two metabolites comprised in the sample obtained from a human test subject.

The term "reference standard" refers to data on metabolic concentrations obtained from a subject (preferably a human subject) of a known diagnostic status. For example, the known diagnostic status may indicate that a subject (preferably a human subject) has no brain tumours, a primary brain tumour and/or a secondary brain tumour. Suitably, the data on metabolic concentrations obtained from the subject for the at least one reference standard are obtained using similar (preferably identical) techniques to the human test subject. The "reference standard" sample is obtained from the same type of biofluid sample as the sample obtained from the human test subject.

The reference standard may comprise (or consist of) a set of data relating to the concentration of said two or more metabolites in a sample or samples derived from a single reference subject, wherein the reference subject is a subject other than the human test subject.

The reference standard may comprise (or consist of) a set of data relating to the concentration of said two or more metabolites in a sample derived from a plurality of (i.e. two or more) reference subjects. Thus, the reference standard may be derived by pooling data obtained from two or more (e.g. three, four, five, 10, 15, 20 or 25, suitably at least 5, preferably 10) reference subjects and calculating an average concentration for each metabolite. Thus, the reference standard may reflect average concentrations of said two or more metabolites in a biofluid in a given population of reference subjects. Said concentrations may be expressed in absolute or relative terms, in the same manner as described above in relation to the sample that is to be tested using a method of the invention.

In a particularly preferred embodiment the reference standard may be obtainable (e.g. obtained) from a non-tumour-bearing subject (e.g. a healthy subject).

The at least one reference standard may be obtained from a tumour bearing subject (preferably a human subject).

Suitably the tumour bearing subject (preferably human subject) may have one or more selected from the group consisting of: a primary brain tumour, a secondary brain tumour, systemic metastases, no metastatic disease, micrometastatic secondary brain tumour and combinations thereof.

The tumour bearing subject (preferably human subject) may have a primary brain tumour. Thus, it can be seen that if there are few differences in the at least two metabolite concentrations between the reference standard obtained from a tumour bearing subject having a primary brain tumour and the human test subject that a diagnosis of the presence of a primary brain tumour can be made. If there are differences (suitably substantial differences) in the at least two metabolite concentrations between the samples then a diagnosis of a lack of the presence of a primary brain tumour can be made.

The tumour bearing subject (preferably human subject) may have a secondary brain tumour. Suitably the secondary brain tumour may be a micrometastatic secondary brain tumour.

Thus, it can be seen that if there are few differences in the at least two metabolite concentrations between the reference standard obtained from a tumour bearing subject having a secondary brain tumour and the human test subject that a diagnosis of the presence of a secondary brain tumour can be made. If there are differences (suitably substantial differences) in the at least two metabolite concentrations between the samples then a diagnosis of the lack of presence of a secondary brain tumour can be made.

The tumour bearing subject (preferably human subject) may have no metastatic disease. In other words the subject may have a primary brain tumour that has not metastasised. Thus, it can be seen that if there are few differences in the at least two metabolite concentrations between the reference standard obtained from a tumour bearing subject not having metastatic disease and the human test subject that a diagnosis of no metastatic disease can be made. If there are differences (suitably substantial differences) in the at least two metabolite concentrations between the samples then a diagnosis of the presence of metastatic disease can be made.

The tumour bearing subject (preferably human subject) may have systemic metastases. Thus, it can be seen that if there are few differences in the at least two metabolite concentrations between the reference standard obtained from a tumour bearing subject having systemic metastases and the human test subject that a diagnosis of systemic metastases can be made. If there are differences (suitably substantial differences) between in the at least two metabolite concentrations between the samples then a diagnosis of the absence of systemic metastases can be made.

The term "systemic metastases" as used herein refers to a subject (preferably a human subject) having secondary tumours in one or more tissues of the body. Preferably the secondary tumours are not and have not been derived from a brain tumour.

The at least one reference standard may be obtained from a non-tumour bearing subject (preferably a human subject). Thus, it can be seen that if there are few differences in the at least two metabolite concentrations between the reference standard obtained from a non-tumour bearing subject and the human test subject that a diagnosis of no brain tumour can be made. If there are differences (suitably substantial differences) in the at least two metabolite concentrations between the samples then a diagnosis of the presence of a brain tumour can be made.

Thus in one embodiment there is provided a method for diagnosing a brain tumour in a human test subject comprising:
a. Determining the concentration of at least two metabolites comprised in a biofluid sample obtained from the human test subject;
b. Comparing the concentration of the at least two metabolites in the biofluid sample with the concentration of the same at least two metabolites in at least one reference standard obtained from a non-tumour bearing subject; and
c. Identifying a concentration difference or no (or substantially no) concentration difference for each of the at least two metabolites in the biofluid sample relative to the reference standard;

wherein: (i) a concentration difference for each of the at least two metabolites in the biofluid sample correlates with the absence of a brain tumour correlates with the presence of a brain tumour; and/or (ii) no (or substantially no) concentration difference for each of the at least two metabolites in the biofluid sample correlates with the absence of a brain tumour.

The term "substantially no concentration difference" may mean a concentration difference that is not statistically significantly different.

Particularly where the method is for differentiating between a primary and a secondary brain tumour the at least one reference standard may be obtained from a subject (preferably a human subject) having a primary brain tumour and/or a secondary brain tumour.

Where the method is for differentiating between a primary and a secondary brain tumour the at least one reference standard may be obtained from a subject (preferably a human subject) having a primary brain tumour. Thus, it can be seen that if there are few differences in the at least two metabolite concentrations between the reference standard obtained from a subject having a primary brain tumour and the human test subject that a diagnosis of a primary brain tumour can be made. If there are differences (suitably substantial differences) in the at least two metabolite concentrations between the samples then a diagnosis of a secondary brain tumour can be made.

Where the method is for differentiating between a primary and a secondary brain tumour the at least one reference standard may be obtained from a subject (preferably a human subject) having a secondary brain tumour (suitably the secondary brain tumour may be a micrometastatic secondary brain tumour). Thus, it can be seen that if there are little or no differences in the at least two metabolite concentrations between the reference standard obtained from a subject having a secondary brain tumour and the human test subject that a diagnosis of a secondary brain tumour can be made. If there are differences (suitably substantial differences) in the at least two metabolite concentrations between the samples then a diagnosis of a primary brain tumour can be made.

Thus in one embodiment there is provided a method for diagnosing a brain tumour in a human test subject comprising:
  a. Determining the concentration of at least two metabolites comprised in a biofluid sample obtained from the human test subject;
  b. Comparing the concentration of the at least two metabolites in the biofluid sample with the concentration of the same at least two metabolites in at least one reference standard obtained from a tumour bearing subject; and
  c. Identifying no (or substantially no) concentration difference for each of the at least two metabolites in the biofluid sample relative to the reference standard;
wherein: (i) a concentration difference for each of the at least two metabolites in the biofluid sample correlates with the absence of a brain tumour correlates with the presence of a brain tumour; and/or (ii) no (or substantially no) concentration difference for each of the at least two metabolites in the biofluid sample correlates with the absence of a brain tumour.

By comparing the concentration of the at least two metabolites in a sample obtained from a human test subject with the concentration of the same at least two metabolites in at least one reference standard obtained from a non-tumour bearing subject and/or a tumour bearing subject or from a subject having a primary or secondary brain tumour and then identifying a concentration difference for the at least two metabolites in the sample relative to the reference standard a determination as to disease state can be made.

The concentration of a metabolite in the diagnostic sample can be expressed in a number of different ways, for example as molar concentration (number of moles of metabolite per unit volume of diagnostic sample) or mass concentration (mass of metabolite per unit volume of diagnostic sample). Alternatively, the concentration of a metabolite can be expressed as parts per million (ppm) or parts per billion (ppb). Such ways of expressing the concentration of a small molecule in solution are known in the art.

Thus, the concentration of a metabolite in the diagnostic sample may be the molar concentration of said metabolite. The concentration of a metabolite in the diagnostic sample may be the mass concentration of said metabolite.

The concentration of a metabolite in the diagnostic sample can be expressed in absolute terms, for example as absolute molar concentration or absolute mass concentration. Alternatively, the concentration of a metabolite in the diagnostic sample can be expressed by comparison to the concentration of a different metabolite in the same sample (i.e. in relative terms). By way of example, the concentration of a metabolite in the diagnostic sample can be normalised by comparison to the concentration of a different reference metabolite within the same diagnostic sample. There is no requirement that the concentration of at least two metabolites be quantitated, for example, the method of the present invention may be carried out by comparing relative concentrations of the at least two metabolites.

The term "diagnostic sample" as used herein refers to a sample that is obtained from a human test subject.

When comparing concentrations between the sample and the reference standard, the way in which the concentrations are expressed is matched between the sample and the reference standard. Thus, an absolute concentration can be compared with an absolute concentration, and a relative concentration can be compared with a relative concentration.

The comparison and/or identification may be carried out using any suitable method known in the art. Any data obtained using the methods of the present invention may be subjected to further analysis such as statistical analysis.

The comparison and/or identification may be carried out using multivariate statistical analysis.

Suitably, the multivariate statistical analysis may be selected from orthogonal partial least squares discriminant analysis (OPLS-DA) as described in the Examples herein or partial least square discriminant analysis (PLS-DA).

Suitably the multivariate statistical analysis may be orthogonal partial least squares discriminant analysis (OPLS-DA) as described in the Examples herein By comparing the concentration of the at least two metabolites in the sample with the concentration of the same at least two metabolites in at least one reference standard obtained from a non-tumour bearing subject and/or a tumour bearing subject; and identifying a concentration difference for each of the at least two metabolites in the sample relative to the reference standard, the concentration difference for each of the at least two metabolites in the sample may correlate with the presence of a brain tumour. Suitably with the presence of a primary brain tumour. Suitably with the presence of a secondary brain tumour. More suitably, a secondary brain tumour at a micrometastatic stage.

By comparing the concentration of the at least two metabolites in the sample with the concentration of the same at least two metabolites in at least one reference standard obtained from a subject having a primary brain tumour and/or a subject having a secondary brain tumour; and identifying a concentration difference for each of the at least two metabolites in the sample relative to the reference standard, the concentration difference for each of the at least two metabolites in the sample may allow differentiation between a primary and a secondary brain tumour. Suitably the secondary brain tumour may be a micrometastatic secondary brain tumour.

The term "concentration difference" embraces both positive and negative differences. Thus, a concentration difference can mean that the concentration of a metabolite is higher in the sample being tested than in the reference standard. Alternatively, a concentration difference can mean that the concentration of a metabolite is lower in the sample than in the reference standard.

The identification of a concentration difference (as described above) can be achieved using methods of statistical analysis. By way of example, NMR spectroscopy can be used to obtain an NMR spectrum for a sample. Methods of statistical analysis (for example, orthogonal partial least squares discriminate analysis [OPLS-DA]), can then be applied to compare said spectrum to an NMR spectrum obtained for a reference standard, allowing the identification of concentration differences.

The metabolite for use in the present invention may change in concentration over time when compared to at least one reference standard. Without wishing to be bound by theory it is believed that the change in concentration over time may be associated with cancer progression and/or stage.

The skilled person can determine the concentration of one or more metabolite(s) in a sample obtained from a human test subject and compare it to the concentration of one or more metabolite(s) in at least one reference standard in order to identify one or more metabolite(s) of interest. Performing this determination will allow the skilled person to determine which of the one or more metabolite(s) has a higher and/or lower concentration with respect to at least one reference standard for each possible diagnosis. For example the skilled person can determine the one or more metabolite(s) has a higher and/or lower concentration in a human test subject with a primary brain tumour, a secondary brain tumour and/or systemic metastasis.

The levels of metabolites discussed below are accurate for a murine model of brain tumour diagnosis, however these values may provide the skilled person with an indication of relevant metabolites for analysing in a sample obtained from a human test subject.

One or more (suitably two or more) of the metabolite(s) creatinine, uric acid, allantoin, 2-oxoglutarate, creatine, phosphocreatine or combinations thereof may be lower in concentration in the human test subject when compared to at least one reference standard.

In one embodiment one or more (suitably two or more) of the metabolite(s) creatinine, uric acid, 2-oxoglutarate, creatine, phosphocreatine or combinations thereof may be lower in concentration in the human test subject when compared to at least one reference standard.

One or more (suitably two or more) of the metabolite(s) $\delta=4.06-4.07$ and/or $\delta=3.03-3.04$, $\delta=5.38-5.39$, $\delta=2.43-2.45$, $\delta=3.93-3.94$ or combinations thereof may be lower in concentration in the human test subject when compared to at least one reference standard.

In one embodiment one or more (suitably two or more) of the metabolite(s) $\delta=4.06-4.07$ and/or $\delta=3.03-3.04$, $\delta=2.43-2.45$, $\delta=3.93-3.94$ or combinations thereof may be lower in concentration in the human test subject when compared to at least one reference standard.

One or more (suitably two or more or three) of the metabolite(s) uric acid, allantoin and/or creatinine may be lower in concentration in the human test subject when compared to at least one reference standard.

In another embodiment one or more of the metabolite(s) uric acid and/or creatinine (suitably creatinine) may be lower in concentration in the human test subject when compared to at least one reference standard.

One or more (suitably two or more) of the metabolite(s) $\delta=5.38-5.39$ and/or $\delta=4.06-4.07$ and/or $\delta=3.03-3.04$ may be lower in concentration in the human test subject when compared to at least one reference standard.

In another embodiment one or more of the metabolite(s) and/or $\delta=4.06-4.07$ and/or $\delta=3.03-3.04$ may be lower in concentration in the human test subject when compared to at least one reference standard.

One or more (suitably two or more) of the metabolite(s) trimethylamine, creatine, phosphocreatine, TMAO, taurine, citrate, 2-oxoglutarate or combinations thereof may be higher in concentration in the human test subject when compared to at least one reference standard.

One or more (suitably two or more) of the metabolite(s) $\delta=2.89-2.90$, $\delta=3.93-3.94$, $\delta=3.27-3.28$, $\delta=3.27-3.44$, $\delta=2.52-2.53$, $\delta=2.43-2.45$, $\delta=2.38$, $\delta=3.11$ or combinations thereof may be higher in concentration in the human test subject when compared to at least one reference standard.

Suitably one or more (suitably two or more) of the metabolite(s) trimethylamine, creatine, phosphocreatine, TMAO, taurine or combinations thereof may be higher in concentration in the human test subject when compared to at least one reference standard.

Suitably one or more (suitably two or more) of the metabolite(s) $\delta=2.89-2.90$, $\delta=3.93-3.94$, $\delta=3.27-3.28$, $\delta=3.27-3.44$, $\delta=2.38$, $\delta=3.11$ or combinations thereof may be higher in concentration in the human test subject when compared to at least one reference standard.

More suitably one or more (suitably two or more) of the metabolite(s) $\delta=2.89-2.90$, $\delta=3.93-3.94$, $\delta=3.27-3.28$, $\delta=3.27-3.44$ or combinations thereof may be higher in concentration in the human test subject when compared to at least one reference standard.

Three or more (suitably four or more or five or more) of the metabolites creatinine, uric acid, allantoin, 2-oxoglutarate, creatine, phosphocreatine or combinations thereof may be lower in concentration in the human test subject when compared to at least one reference standard.

In one embodiment three or more (suitably four or more, e.g. five) of the metabolites creatinine, uric acid, 2-oxoglutarate, creatine, phosphocreatine or combinations thereof may be lower in concentration in the human test subject when compared to at least one reference standard.

Three or more (suitably four or more, e.g. five) of the metabolites $\delta=4.06-4.07$ and/or $\delta=3.03-3.04$, $\delta=5.38-5.39$, $\delta=2.43-2.45$, $\delta=3.93-3.94$ or combinations thereof may be lower in concentration in the human test subject when compared to at least one reference standard.

In another embodiment three or more (e.g. four) of the metabolites $\delta=4.06-4.07$ and/or $\delta=3.03-3.04$, $\delta=2.43-2.45$, $\delta=3.93-3.94$ or combinations thereof may be lower in concentration in the human test subject when compared to at least one reference standard.

Suitably the metabolites uric acid, allantoin and/or creatinine may be lower in concentration in the human test subject when compared to at least one reference standard.

Suitably the metabolites uric acid, and/or creatinine may be lower in concentration in the human test subject when compared to at least one reference standard. Preferably creatinine may be lower in concentration in a human test subject when compared to at least one reference standard (e.g. from a non-tumour bearing subject).

Three or more (suitably four or more or five or more) of the metabolites trimethylamine, creatine, phosphocreatine, TMAO, taurine, citrate, 2-oxoglutarate or combinations thereof may be at a higher concentration in the human test subject when compared to at least one reference standard.

Three or more (suitably four or more or five or more) of the metabolites $\delta=2.89$-$2.90$, $\delta=3.93$-$3.94$, $\delta=3.27$-$3.28$, $\delta=3.27$-$3.44$, $\delta=2.52$-$2.53$, $\delta=2.43$-$2.45$, $\delta=2.38$, $\delta=3.11$ or combinations thereof may be higher in concentration in the human test subject when compared to at least one reference standard.

Suitably three or more (suitably four or more or five) of the metabolite(s) trimethylamine, creatine, phosphocreatine, TMAO, taurine or combinations thereof may be higher in concentration in the human test subject when compared to at least one reference standard.

Suitably three or more (suitably four or more or five or more) of the metabolites $\delta=2.89$-$2.90$, $\delta=3.93$-$3.94$, $\delta=3.27$-$3.28$, $\delta=3.27$-$3.44$, $\delta=2.38$, $\delta=3.11$ or combinations thereof may be higher in concentration in the human test subject when compared to at least one reference standard.

More suitably three or more (suitably four) of the metabolites $\delta=2.89$-$2.90$, $\delta=3.93$-$3.94$, $\delta=3.27$-$3.28$, $\delta=3.27$-$3.44$ or combinations thereof may be higher in concentration in the human test subject when compared to at least one reference standard.

An unidentified metabolite having a triplet centred at $\delta=2.38$ may be lower in concentration when compared to at least one reference standard. Suitably the at least one reference standard may be obtained from a non-tumour bearing subject.

An unidentified metabolite having a doublet centred at $\delta=3.11$ may be lower in concentration when compared to at least one reference standard. Suitably the at least one reference standard may be obtained from a non-tumour bearing subject.

The concentration of the metabolites citrate and/or 2-oxoglutarate may be higher when compared to the at least one reference standard at the later stages of tumour development. Suitably the at least one reference standard may be obtained from a non-tumour bearing subject.

The metabolite 2-oxoglutarate may be lower in the early stages of tumour development and then higher when compared to the at least one reference standard in later stages of tumour development. Suitably the at least one reference standard may be obtained from a non-tumour bearing subject.

The concentration of the metabolites citrate and/or 2-oxoglutarate may remain substantially unchanged when compared to the at least one reference standard at the early stages of tumour development. Suitably the at least one reference standard may be obtained from a non-tumour bearing subject.

The concentration of the metabolites TMA, TMAO, creatine, phosphocreatine, taurine or combinations thereof may be higher when compared to the at least one reference standard at the early stages of tumour development. Suitably the at least one reference standard may be obtained from a non-tumour bearing subject.

Suitably the metabolites TMA, TMAO, taurine or combinations thereof may be higher in concentration when compared to the at least one reference standard at the early stages of tumour development. Suitably the at least one reference standard may be obtained from a non-tumour bearing subject.

The concentration of metabolites TMA, TMAO, creatine, phosphocreatine, taurine or combinations thereof may later return to baseline values when compared to at least one reference standard at the later stages of tumour development. Suitably the at least one reference standard may be obtained from a non-tumour bearing subject.

The concentration of the metabolites creatinine, uric acid and/or allantoin may be lower at the later stages of tumour development when compared to at least one reference standard. Suitably the at least one reference standard may be obtained from a non-tumour bearing subject.

The concentration of the metabolites $\delta=2.52$-$2.53$ and/or $\delta=2.43$-$2.45$ may be higher when compared to the at least one reference standard at the later stages of tumour development. Suitably the at least one reference standard may be obtained from a non-tumour bearing subject.

The metabolite $\delta=2.43$-$2.45$ may be lower in the early stages of tumour development and then higher when compared to the at least one reference standard in later stages of tumour development. Suitably the at least one reference standard may be obtained from a non-tumour bearing subject.

The concentration of the metabolites $\delta=2.52$-$2.53$ and/or $\delta=2.43$-$2.45$ may remain substantially unchanged when compared to the at least one reference standard at the early stages of tumour development. Suitably the at least one reference standard may be obtained from a non-tumour bearing subject.

The concentration of the metabolites $\delta=2.89$-$2.90$, $\delta=3.27$-$3.28$, $\delta=3.93$-$3.94$, $\delta=3.27$-$3.44$ or combinations thereof may be higher when compared to the at least one reference standard at the early stages of tumour development. Suitably the at least one reference standard may be obtained from a non-tumour bearing subject.

Suitably the metabolites $\delta=2.89$-$2.90$, $\delta=3.27$-$3.28$, $\delta=3.27$-$3.44$ or combinations thereof may be higher in concentration when compared to the at least one reference standard at the early stages of tumour development. Suitably the at least one reference standard may be obtained from a non-tumour bearing subject.

The concentration of metabolites $\delta=2.89$-$2.90$, $\delta=3.27$-$3.28$, $\delta=3.93$-$3.94$, $\delta=3.27$-$3.44$ or combinations thereof may later return to baseline values when compared to at least one reference standard at the later stages of tumour development. Suitably the at least one reference standard may be obtained from a non-tumour bearing subject.

The concentration of the metabolites $\delta=4.06$-$4.07$ and/or $\delta=3.03$-$3.04$ and/or $\delta=5.38$-$5.39$ may be lower at the later stages of tumour development when compared to at least one reference standard. Suitably the at least one reference standard may be obtained from a non-tumour bearing subject.

In another embodiment the concentration of the metabolites $\delta=4.06$-$4.07$ and/or $\delta=3.03$-$3.04$ may be lower at the later stages of tumour development when compared to at least one reference standard. Suitably the at least one reference standard may be obtained from a non-tumour bearing subject.

The term "early stages of tumour development" as used herein means a stage at which the tumour is less than about 1.3 mm in size, suitably less than about 1.0 mm in size. The detection of metabolites that have a concentration that is higher or lower at the early stages of tumour development may be indicative of an early stage brain tumour, suitably an early stage secondary brain tumour, preferably a micrometastatic secondary brain tumour.

Advantageously, analysis of such metabolites may allow for early-stage diagnosis and/or differentiation between a primary or secondary brain tumour in a human test subject.

The term "later stages of tumour development" as used herein means more than about 1.0 mm in size, suitably more than about 1.3 mm, 1.5 mm or 2 mm in size. The detection of metabolites that have a concentration that is higher or lower at the later stages of tumour development may be indicative of a late stage brain tumour, suitably a late stage primary brain tumour or secondary brain tumour.

The concentration of uric acid and/or allantoin may be lower by at least about 1%, 5% or 10% (preferably at least about 20%) when compared to the concentration of uric acid and/or allantoin comprised in a sample obtained from at least one reference standard from a non-tumour bearing subject. Suitably the concentration may be lower after the beginning of tumour development.

The concentration of citrate may be higher by at least about 1%, 5% or 15% (preferably at least about 30%) when compared to the concentration of citrate comprised in a sample obtained from at least one reference standard from a non-tumour bearing subject. Suitably the concentration may be higher after the beginning of tumour development.

The concentration of TMAO may be higher by at least about 5% or 10% (preferably at least about 15%) when compared to the concentration of TMAO comprised in a sample obtained from at least one reference standard from a non-tumour bearing subject. Suitably the concentration may be higher when the tumour is between about 0.1 mm to about 1.5 mm (suitably when the tumour is between about 0.5 mm to about 1.25 mm in size).

The concentration of 2-oxoglutarate may be higher by at least about 1%, 5% or 15% (preferably at least about 30% or 40%) when compared to the concentration of citrate comprised in a sample obtained from at least one reference standard from a non-tumour bearing subject. Suitably concentration may be higher at the beginning of tumour development.

The concentration of creatinine may be lower by at least about 5%, 15% or 20% (preferably at least about 30%) when compared to the concentration of creatinine comprised in a sample obtained from at least one reference standard from a non-tumour bearing subject. Suitably the concentration may be higher after the beginning of tumour development.

The concentration of TMA may be higher by at least about 5%, 15% or 30% (preferably at least about 40%) when compared to the concentration of TMA comprised in a sample obtained from at least one reference standard from a non-tumour bearing subject. Suitably the concentration may be higher when the size of the tumour is between about 0.1 mm to about 1.7 mm (suitably between about 0.5 mm to about 1.5 mm in size).

The concentration of creatine may be higher by at least about 5%, 15% or 30% (preferably at least about 40%) when compared to the concentration of creatine comprised in a sample obtained from at least one reference standard from a non-tumour bearing subject. Suitably the concentration may be higher when the size of the tumour is between about 0.1 mm to about 1.7 mm (suitably between about 0.5 mm to about 1.5 mm in size).

The concentration of phosphocreatine may be higher by at least about 5%, 15% or 30% (preferably at least about 40%) when compared to the concentration of creatine comprised in a sample obtained from at least one reference standard from a non-tumour bearing subject. Suitably the concentration may be higher when the size of the tumour is between about 0.1 mm to about 1.7 mm (suitably between about 0.5 mm to about 1.5 mm in size).

The concentration of taurine may be higher by at least about 1%, 5% or 10% (preferably at least about 20%) when compared to the concentration of creatine comprised in a sample obtained from at least one reference standard from a non-tumour bearing subject. Suitably the concentration may be higher when the size of the tumour is between about 0.1 mm to about 1.9 mm (suitably between about 0.5 mm to about 1.7 mm in size).

The indications above with respect to stage and/or size of tumours are based on a murine model. These values may be similar for a one or more metabolite(s) analysed in a sample obtained from a human test subject. The skilled person will appreciate that by comparing a sample obtained from a human test subject with at least one reference standard obtained from a subject with a tumour of known progression/stage that the equivalent metabolite concentrations in respect of tumour size and/or stage can be determined.

Comparing and identifying a difference in concentration of at least two metabolites comprised in the sample obtained from a human test subject with at least one reference standard (preferably at least one reference standard obtained from a non-tumour bearing subject) may allow the diagnosis of a brain tumour or a secondary brain tumour or the distinction between a brain tumour or a secondary brain tumour compared to systemic metastases or an absence of a brain tumour.

Therefore measuring the concentration of at least one metabolite selected from the group consisting of: TMAO, TMA, taurine, 2-oxoglutarate, uric acid, allantoin, phosphocreatine, creatine and an unidentified metabolite having a triplet at $\delta=2.38$ or combinations thereof may allow the diagnosis of a brain tumour or a secondary brain tumour or the distinction between a brain tumour or a secondary brain tumour compared to systemic metastases or an absence of a brain tumour.

In another embodiment measuring the concentration of at least one metabolite selected from the group consisting of: TMAO, TMA, taurine, 2-oxoglutarate, uric acid, phosphocreatine, creatine and an unidentified metabolite having a triplet at $\delta=2.38$ or combinations thereof may allow the diagnosis of a brain tumour or a secondary brain tumour or the distinction between a brain tumour or a secondary brain tumour compared to systemic metastases or an absence of a brain tumour.

The skilled person can determine the concentration of one or more metabolite(s) in a sample obtained from a human test subject and compare it to the concentration of one or more metabolite(s) in at least one reference standard in order to identify one or more metabolite(s) of interest. Performing this determination will allow the skilled person to determine which of the one or more metabolite(s) has a higher and/or lower concentration with respect to at least one reference standard for each possible diagnosis. For example the skilled person can determine the one or more metabolite(s) has a higher and/or lower concentration in a human test subject with a primary brain tumour, a secondary brain tumour and/or systemic metastasis. Additionally, the skilled person may be able to determine the absolute and/or relative differences in concentration of one or more metabolite(s) based on a comparison of the differences between the sample obtained from a human test subject and the at least one reference standard.

The levels of metabolites discussed below are accurate for a murine model of brain tumour diagnosis, however this model is believed to have similar predictive value in a human test subject. These values may therefore provide the skilled person with an indication of relevant metabolites for analysis of a sample obtained from a human test subject.

A diagnosis of a secondary brain tumour may be made if the concentration of: (i) one or more of TMAO, taurine, creatine, phosphocreatine or TMA is higher; and/or (ii) one or more of uric acid, allantoin, an unidentified metabolite having a triplet at δ=2.38 or an unidentified metabolite having a doublet at δ=3.11 is lower; when compared to at least one reference standard obtained from a subject with systemic metastases.

In another embodiment diagnosis of a secondary brain tumour may be made if the concentration of: (i) one or more of TMAO, taurine, creatine, phosphocreatine or TMA is higher; and/or (ii) one or more of uric acid, an unidentified metabolite having a triplet at δ=2.38 or an unidentified metabolite having a doublet at δ=3.11 is lower; when compared to at least one reference standard obtained from a subject with systemic metastases.

A diagnosis of a secondary brain tumour may be made if the concentration of: (i) one or more of TMAO, taurine, creatine, phosphocreatine or TMA is higher; and/or (ii) one or more of uric acid, allantoin, or an unidentified metabolite having a triplet at δ=2.38 is lower; when compared to at least one reference standard obtained from a subject with systemic metastases.

In a further embodiment diagnosis of a secondary brain tumour may be made if the concentration of: (i) one or more of TMAO, taurine, creatine, phosphocreatine or TMA is higher; and/or (ii) one or more of uric acid, or an unidentified metabolite having a triplet at δ=2.38 is lower; when compared to at least one reference standard obtained from a subject with systemic metastases.

The diagnosis of a secondary brain tumour may be made if the concentration of one or more of TMAO, taurine, creatine, phosphocreatine or TMA is higher; when compared to at least one reference standard obtained from a subject with systemic metastases.

The diagnosis of a secondary brain tumour may be made if the concentration of one or more of uric acid, allantoin, an unidentified metabolite having a triplet at δ=2.38 or an unidentified metabolite having a doublet at δ=3.11 is lower; when compared to at least one reference standard obtained from a subject with systemic metastases.

In one embodiment the diagnosis of a secondary brain tumour may be made if the concentration of one or more of uric acid, an unidentified metabolite having a triplet at δ=2.38 or an unidentified metabolite having a doublet at δ=3.11 is lower; when compared to at least one reference standard obtained from a subject with systemic metastases.

The diagnosis of a secondary brain tumour may be made if the concentration of one or more of uric acid, allantoin, or an unidentified metabolite having a triplet at δ=2.38 is lower; when compared to at least one reference standard obtained from a subject with systemic metastases.

In another embodiment the diagnosis of a secondary brain tumour may be made if the concentration of one or more of uric acid, or an unidentified metabolite having a triplet at δ=2.38 is lower; when compared to at least one reference standard obtained from a subject with systemic metastases.

Preferably the concentration of uric acid and/or allantoin (suitably uric acid) may be lower when compared to at least one reference standard obtained from a subject with systemic metastases.

Preferably the concentration changes indicated above may be indicative of a measurement at the beginning of tumour development.

Suitably the concentration of TMAO may be higher in a sample obtained from a human test subject having a secondary brain tumour by at least about 5% or 10% (preferably at least about 20%) when compared to at least one reference standard obtained from a subject having systemic metastases.

Suitably the concentration of taurine may be higher in a sample obtained from a human test subject having a secondary brain tumour by at least about 5%, 10% or 20% (preferably at least 30%) when compared to at least one reference standard obtained from a subject having systemic metastases.

Suitably the concentration of taurine may be lower in a sample obtained from a human test subject having a secondary brain tumour by at least about 5%, 10% or 20% (preferably at least 30%) when compared to at least one reference standard obtained from a subject having systemic metastases.

Suitably the concentration of creatine may be higher in a sample obtained from a human test subject having a secondary brain tumour by at least about 5%, 10% or 20% (preferably at least 30%) when compared to at least one reference standard obtained from a subject having systemic metastases.

Suitably the concentration of phosphocreatine may be higher in a sample obtained from a human test subject having a secondary brain tumour by at least about 5%, 10% or 20% (preferably at least 30%) when compared to at least one reference standard obtained from a subject having systemic metastases.

Suitably the concentration of TMA may be higher in a sample obtained from a human test subject having a secondary brain tumour by at least about 5%, 10% or 20% (preferably at least 30%) when compared to at least one reference standard obtained from a subject having systemic metastases.

Suitably the concentration of uric acid and/or allantoin (suitably uric acid) may be lower in a sample obtained from a human test subject having a secondary brain tumour by at least about 1%, 5% or 10% (preferably at least 20%) when compared to at least one reference standard obtained from a subject having systemic metastases.

Suitably the concentration of an unidentified metabolite having a triplet at δ=2.38 may be lower in a sample obtained from a human test subject having a secondary brain tumour by at least about 1% (preferably at least 2%) when compared to at least one reference standard obtained from a subject having systemic metastases.

Suitably the concentration of an unidentified metabolite having a triplet at δ=2.38 may be higher in a sample obtained from a human test subject having systemic metastases by at least about 5% or 10% (preferably by at least 20%) when compared to at least one reference standard obtained from a subject having a secondary brain tumour.

Suitably the concentration of an unidentified metabolite having a doublet at δ=3.11 may be lower in a sample obtained from a human test subject having a secondary brain tumour by at least about 1% or 5% (preferably at least 10%) when compared to at least one reference standard obtained from a subject having systemic metastases.

The skilled person will understand from the teaching above that in order to diagnose a subject having systemic metastases then the inverse is true. For example if phosphocreatine may be higher in concentration in a sample obtained from a human test subject having a secondary brain tumour by at least about 5%, 10% or 20% (preferably at least 30%) when compared to at least one reference standard obtained from a subject having systemic metastases, then a lower phosphocreatine concentration when compared to at least one reference standard obtained from a subject having a secondary brain tumour will allow the diagnosis of systemic metastases. Likewise if the concentrations of metabolites in the sample obtained from a human test subject are similar or the same as those for at least one reference sample obtained from a subject having a primary brain tumour then a diagnosis of a primary brain tumour can be made, or if similar or the same as at least one reference sample obtained from a subject having a secondary brain tumour then a diagnosis of a secondary brain tumour can be made or if similar or the same as at least one reference sample obtained from a subject having systemic metastases then a diagnosis of a secondary brain tumour can be made.

Suitably a diagnosis that a human test subject has a brain tumour may be determined by comparing the concentration of: (i) TMAO, creatine, phosphocreatine or combinations thereof; and (ii) uric acid, allantoin, creatinine or combinations thereof. Suitably the concentration of TMAO, creatine, phosphocreatine or combinations thereof may be higher, whilst the concentration of uric acid, allantoin, creatinine or combinations thereof may be lower. Preferably the reference standard used in such a diagnosis may be a reference standard from a non-tumour bearing subject.

In another embodiment suitably a diagnosis that a human test subject has a brain tumour may be determined by comparing the concentration of: (i) TMAO, creatine, phosphocreatine or combinations thereof; and (ii) uric acid, creatinine or combinations thereof. Suitably the concentration of TMAO, creatine, phosphocreatine or combinations thereof may be higher, whilst the concentration of uric acid, creatinine or combinations thereof may be lower. Preferably the reference standard used in such a diagnosis may be a reference standard from a non-tumour bearing subject.

Suitably the concentration of TMAO may be higher by at least about 5% or 10% (more suitably at least about 15%) when compared to at least one reference standard having systemic metastases or no brain tumour.

Suitably the concentration of creatine may be higher by at least about 10% or 20% (more suitably at least about 30%) when compared to at least one reference standard having systemic metastases or no brain tumour.

Suitably the concentration of phosphocreatine may be higher by at least about 10% or 20% (more suitably at least about 30%) when compared to at least one reference standard having systemic metastases or no brain tumour.

Suitably the concentration of uric acid and/or allantoin may be lower by at least about 5% or 10% (more suitably at least about 15%) when compared to at least one reference standard having systemic metastases or no brain tumour.

More preferably a diagnosis that a human test subject has a brain tumour may be determined by comparing the concentration of: (i) TMAO, creatine and phosphocreatine; and (ii) uric acid, allantoin and creatinine.

More preferably a diagnosis that a human test subject has a brain tumour may be determined by comparing the concentration of: (i) TMAO, creatine and phosphocreatine; and (ii) uric acid, and creatinine.

Preferably the concentration of TMAO, creatine and phosphocreatine may be higher whilst the concentration of uric acid and/or allantoin and creatinine may be lower.

Suitably the concentration of TMAO may be higher by at least about 5% or 10% (more suitably at least about 15%) when compared to at least one reference standard having systemic metastases or no brain tumour.

Suitably the concentration of creatine may be higher by at least about 10% or 20% (more suitably at least about 30%) when compared to at least one reference standard having systemic metastases or no brain tumour.

Suitably the concentration of phosphocreatine may be higher by at least about 10% or 20% (more suitably at least about 30%) when compared to at least one reference standard having systemic metastases or no brain tumour.

Suitably the concentration of uric acid and/or allantoin may be lower by at least about 5% or 10% (more suitably at least about 15%) when compared to at least one reference standard having systemic metastases or no brain tumour.

The ratio of creatine and/or phosphocreatine to uric acid and/or allantoin may allow the diagnosis of a brain tumour (e.g. a secondary brain tumour) or the distinction between a brain tumour compared to non-brain tumours or systemic metastases.

A high concentration of TMA in a sample obtained from a human test subject may be indicative of a secondary brain tumour when compared to at least one reference standard obtained from a subject having systemic metastases.

Suitably the concentration of TMA in a sample obtained from a human test subject may be higher by at least about 10%, 30% or 50% (more suitably at least about 70%) when compared to at least one reference standard obtained from a subject having systemic metastases.

The method of the invention may further comprise recording the output of at least one step on a data-storage medium. By way of example, the method of the present invention can generate data relating to the human test subject and/or at least one reference standard obtained from a subject, such data being recordable on a data-storage medium (for example, a form of computer memory such as a hard disk, compact disc, floppy disk, or solid state drive). Such data may comprise (or consist of) data relating to the concentration in a sample (from said human test subject or subject from which the at least one reference standard is obtained) of any of said two or more metabolites (as described) above.

The invention provides a data-storage medium comprising data obtained by any of the methods of the invention.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

The headings provided herein are not limitations of the various aspects or embodiments of this disclosure which can be had by reference to the specification as a whole. Accordingly, the terms defined immediately below are more fully defined by reference to the specification as a whole.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a metabolite" includes a plurality of such candidate agents and reference to "the tumour" includes reference to one or more tumours and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

BRIEF DESCRIPTION OF THE DRAWINGS

The invention will now be described, by way of example only, with reference to the following Figures and Examples, in which.

EXAMPLES

Figure 1:
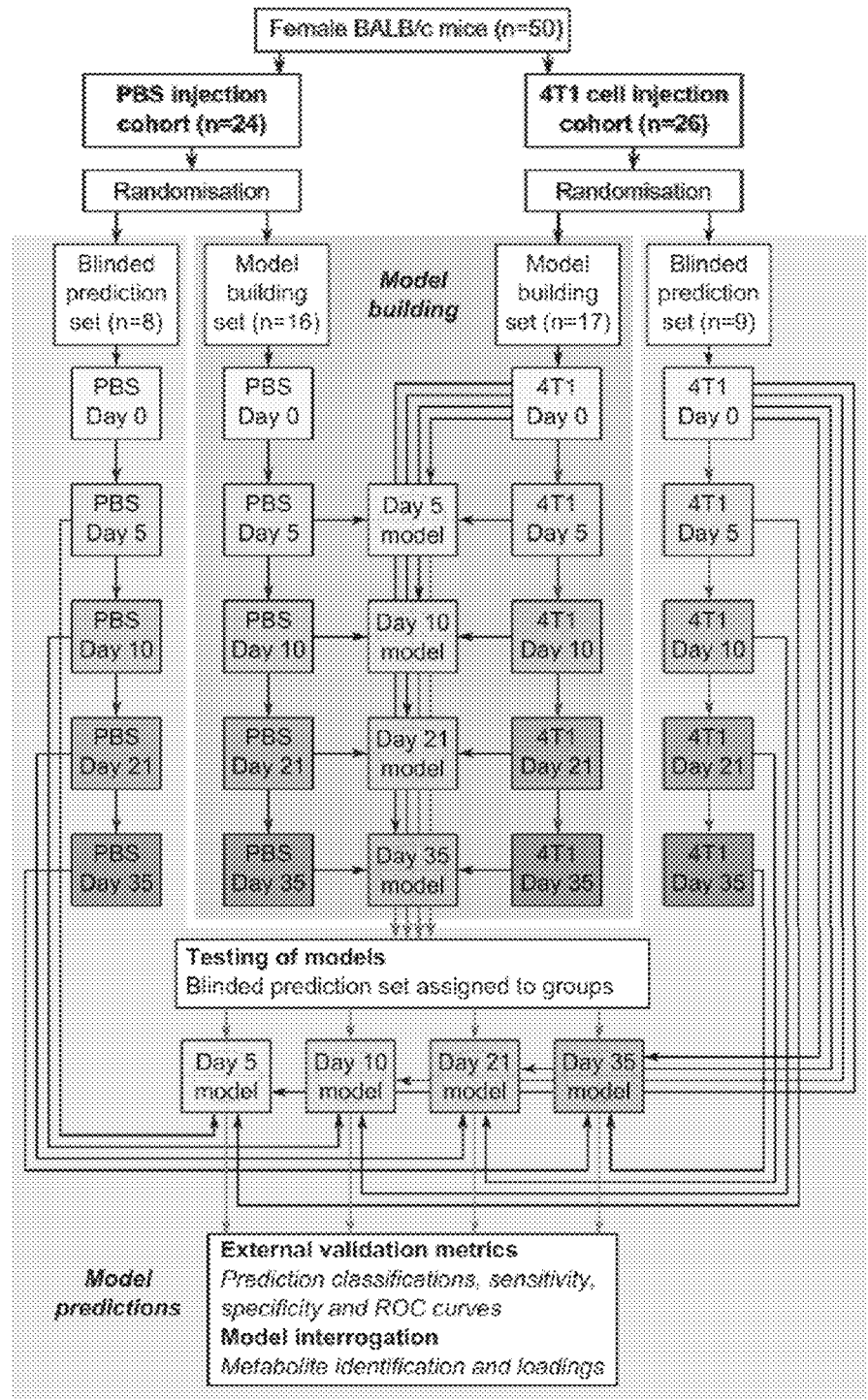
FIG. 1 shows a flowchart of study design for the intracerebral brain metastasis model. Both 4T1-GFP cell-injected and PBS-injected cohorts were split into two groups, one for model building and one reserved as a blinded testing set. Each model is then constructed comparing 4T1-GFP animals from a particular day with the control set comprising PBS-injected animals from the same day as well as the naïve 4T1-GFP animal samples from before injection.

It remains a clinically intractable problem to diagnose patients with brain metastases at an early time point. There are possible strategies to predict the probability that a patient will develop a brain metastasis, e.g. through the use of a nomogram (Graesslin et al. 2010). However, these strategies would work only for identifying high risk patients, not for final diagnosis. Urinary metabolomics has been shown to be a powerful screening approach to separate diseased individuals from controls e.g. in Barrett's oesophagus and oesophageal carcinoma (Davis et al. 2012) or separating oral squamous cell carcinomas from oral leukoplakia patients from control groups (Xie et al. 2012) but neither of these studies included a separate validation cohort leaving open the possibility of co-incidence in their models. The present inventors have shown that models can be built using urine samples from animals with known brain or systemic metastatic loads and then used to sensitively and specifically predict completely unknown sample group membership.

The development of new methods for earlier detection of brain metastases is critical for improved survival in patients with metastatic spread to the brain. Here the present inventors have found that it is possible to reliably separate mice with focal brain metastases from control mice as early as five days after induction of tumours, on the basis of urine $^1$H NMR analysis coupled with a multivariate statistical pattern recognition approach (OPLS-DA). The models separating tumour-bearing animals from control animals increased in strength throughout the timecourse. It was also possible to separate animals injected with 4T1-GFP cells via either the intracardiac or intravenous routes, which give rise to differing systemic or CNS metastatic burdens, from control cohorts. Together, these findings suggest that this biofluid-based metabolomics approach could have considerable utility in detection of brain metastases earlier than currently used clinical approaches.

Materials & Methods

Animal Models

Intracerebral 4T1-GFP Model

Female BALB/c mice (6-7 weeks) were housed under a standard 12 h light 12 h dark cycle and with access to standard chow and water ad libitum. For surgery, animals (n=50) were anaesthetised with isoflurane (1.5-2.0%) in a mixture of oxygen and nitrous oxide (30:70%) and placed in a stereotaxic frame. The skull was exposed and a burr-hole drilled above the injection site. A finely drawn glass microcannula, tip diameter ca. 75 μm was inserted into the left striatum (coordinates relative to bregma: +0.5 mm; left 1.9 mm; depth 2.9 mm). Over a 5 min period, animals were injected with either cells (n=26) or vehicle alone (n=24). Cell-injected animals received 5000 4T1-GFP cells (a metastasising murine mammary carcinoma cell line) in 0.5 µL phosphate-buffered saline (PBS) vehicle. The microcannula was left in place for 5 minutes, raised by 0.5 mm and left for a further 2 minutes before complete removal. The scalp wound was closed and the animals were assessed daily for weight and clinical score.

Urine samples were collected by handling the mice over a clean impermeable surface, both before tumour induction and at days 5, 10, 21 and 35 post-tumour induction. Samples contaminated with faecal material were not used. Urine samples were frozen on dry ice and stored at −80° C. until NMR spectroscopy was performed.

Systemically-Induced 4T1-GFP Models

To investigate differing systemic and CNS metastatic burdens, two further groups of animals were injected either intracardially or intravenously with 4T1-GFP cells. In the case of intravenous injections, the highest tumour burden is found in the lungs, the site of the first capillary bed after the injection point. In the case of the intracardiac route, tumours are found systemically including in the brain. For both models urine samples were obtained at day 0, prior to injection, and day 10 post-injection (n=20 per group). For the intracardiac group, female BALB/c mice (6-7 weeks) were anaesthetised as described above. The hair covering the thoracic cavity on the left side of the heart was removed by clipping followed by application of depilatory cream (Veet, Boots, UK). The depilated area was coated with ultrasound gel and the left ventricle of the heart located with the aid of ultrasound imaging. A 27 gauge needle was used to inject $1\times10^5$ 4T1 cells into the left ventricle of the heart in 100 µL sterile PBS. The animals were allowed to recover in a heated chamber and were assessed daily for weight and clinical score. For the intravenous group, awake, restrained female BALB/c mice (6-7 weeks) were injected via a tail vein with $1\times10^5$ 4T1 cells in 100 µL sterile PBS. Control groups of age-matched animals injected via the appropriate route with sterile PBS were included (n=6 per group).

Histological Analysis

Following final sample collection, all animals were transcardially perfused with heparinised saline followed by 50 mL of PLP-light (PLP with 0.025% w/v glutaraldehyde). After perfusion, the brains were dissected, post-fixed in PLP-light, cryoprotected, embedded and frozen in isopentane at −80° C. For immunohistochemical detection of tumours, 20 µm sections were quenched with 1% (v/v) hydrogen peroxide (30% w/v, Sigma Aldrich, UK) in methanol and blocked with 1% normal rabbit serum (Vector Laboratories, Burlingame, Calif., USA) in PBS for 1 h. Sections were incubated with primary chicken anti-GFP antibody (Abcam, UK; 1:1000, 4° C., overnight), washed using PBS+0.01% (v/v) Tween-20 (Sigma Aldrich, UK), then incubated with a biotinylated polyclonal rabbit anti-chicken IgY secondary antibody (Abcam, UK; 1:1000, 1 h). Slides were washed then incubated with VECTASTAIN Elite ABC kit (Vector labs, UK; 1:1:100, 45 min). The peroxidase was visualized using 3,3'-diaminobenzidine (DAB; Sigma Aldrich, UK). Sections were counterstained with cresyl violet (Sigma Aldrich, UK), dehydrated and mounted. All incubations were performed at room temperature, unless otherwise stated. Slides were scanned using a ScanScope slide scanner at 200× magnification and tumours and brain sections were manually delineated to quantify area and number.

NMR Spectroscopy

Urine samples were defrosted on ice and 50 µL from each was placed in a 5 mm NMR tube and diluted to a final volume of 600 µL with phosphate buffer (0.24M sodium phosphate, pH 7.4, 0.1% sodium azide, 0.8% sodium chloride) in $D_2O$ containing 1 mM TSP (3-trimethylsilyl-1-[2,2,3,3,-$^2H_4$] propionate) as an internal standard. $^1H$ NMR spectra were acquired for each sample at 700 MHz (Bruker Avance III spectrometer equipped with a $^1H$ TCI cryoprobe, Bruker, Coventry, UK). For all samples a 1D NOESY pre-saturation sequence, with solvent pre-saturation during the relaxation delay (2 s) and mixing time (10 ms) was used. Two dimensional $^1H$ NMR spectra were acquired from a single sample within each group to assist with metabolite identification. The 2D correlation spectroscopy (COSY) spectra were acquired on the same spectrometer as the 1D NMR spectra. The COSY spectra were acquired with 1.5 s solvent presaturation, a spectral width of 10 ppm (7002 Hz), and 16 or 32 transients per $t_1$ increment for 256 increments. All NMR experiments were conducted at 293K.

NMR Data Pre-Processing

The 1D $^1H$ plasma spectra were imported into Matlab (MathWorks, Nantick, USA) using the RBNMR script then automatically phased using a method optimised for signal-dense spectra (Bao et al. 2013). Spectra with gross distortions or phasing anomalies were excluded at this stage. Spectra were baseline corrected using a $3^{rd}$ order polynomial fitted to regions without peaks (Beek 2007) then aligned to the TSP peak at 0 ppm. Spectra were unit-scaled to the summed spectrum integral, excluding the water and TSP peak regions. Coarsely aligned spectra were then refined by non-linear warping to account for subtle peak shifts arising from differing sample pH, ionic strength etc. (Skov et al. 2006). Aligned spectra were sub-divided into 0.01 ppm regions (δ=start of integral region) from 0.2 to 9.6 ppm and integrated to yield 940 independent variables for each sample. The regions covering the variable water peak (4.7 to 5.0 ppm) and urea peak (5.70 to 5.95 ppm) were excluded along with the region covering a contaminant methanol peak (3.35 to 3.38 ppm). Thus, modelling was conducted with 882 variables for each sample.

Multivariate Statistical Modelling

OPLS-DA modelling was conducted using SIMCA 13.0 (Umetrics, Sweden) to produce models which maximally separated groups of spectra. For the 4T1-GFP cell time-course, four models were constructed to separate samples from mice at day 5, 10, 21 or 35 from their respective control cohorts. The control cohorts included samples from the 4T1-GFP injected mice before they were injected with cells on day 0, as well as samples from age- and timepoint-matched mice injected with PBS alone (see study schematic in FIG. 1). The inclusion of these two groups in the control cohort allows adequate control of both differences between batches of mice as well as the effect of the injection procedure itself. Any remaining differences are thus attributable to the presence of the tumour alone.

All data were centred and scaled using Pareto variance in order to suppress the noise present. To determine the potential predictive value of the models, the $q^2$ value for each model was calculated. The $q^2$ of a model is derived from a step-wise removal of a fraction of samples and a prediction of the group membership of the removed samples using a model built with the remaining samples. A $q^2>0$ means that the model is predictive and a $q^2>0.4$ is considered statistically significant (Waterman et al. 2010). Cross-validation (CV)-ANOVA p-values for each model were determined with p-values <0.05 being considered significant.

To test the predictive ability of key models, independent testing sets of spectra obtained from samples from additional animals (FIG. 1) were produced. The models were tested by introducing these new spectra in a random fashion and allowing the model to predict group membership. These results are presented as 2×2 contingency tables and ROC curves with Fisher's exact statistic calculated in each case.

Metabolite Identification and Quantification

In order to identify the metabolites underpinning model separations, each model's variable importance in projection (VIP) plots was consulted and variables with a VIP score >2 were considered have the greatest impact. Comparison of important bucket integrals by ANOVA followed by Dunnett's multiple comparison tests allowed determination of direction, magnitude and significance of metabolite changes between groups. Peaks present in important buckets were identified using a combination of COSY NMR, literature values and reference to the human metabolome database (Fan 1996, Beckonert et al. 2007, Gronwald et al. 2011, Wishart et al. 2013). Further confirmation of the metabolites was achieved by examining the J-coupling (spin-spin interactions between neighbouring hydrogens) of the resonances within the spectra.

Quantification of specific metabolites of interest was performed by summing the integral regions of each metabolite as they contributed to the models. This yields a relative quantification which allows comparison to be made across the time course and relative to control but without yielding absolute concentrations. Significance of relative changes in metabolite concentration were determined by 1-way ANOVA followed by Dunnet's multiple comparison post-hoc test comparing each timepoint to the control group. p values <0.05 were considered significant.

Example 1

Intracerebral 4T1-GFP Model Timecourse

A focal area of metastatic colonies was induced in the striatum of mice injected intracerebrally with the 4T1-GFP cells. Tumours initially grew very focally before beginning to disseminate from the injection site, by days 21 and 35, by growing adjacent to vessels along the perivascular niche, as described previously (Serres et al. 2012). Mice showed no significant clinical signs or weight loss throughout the experimental time course.

Intracerebral 4T1-GFP Urine Analysis and Modelling

Figure 2:
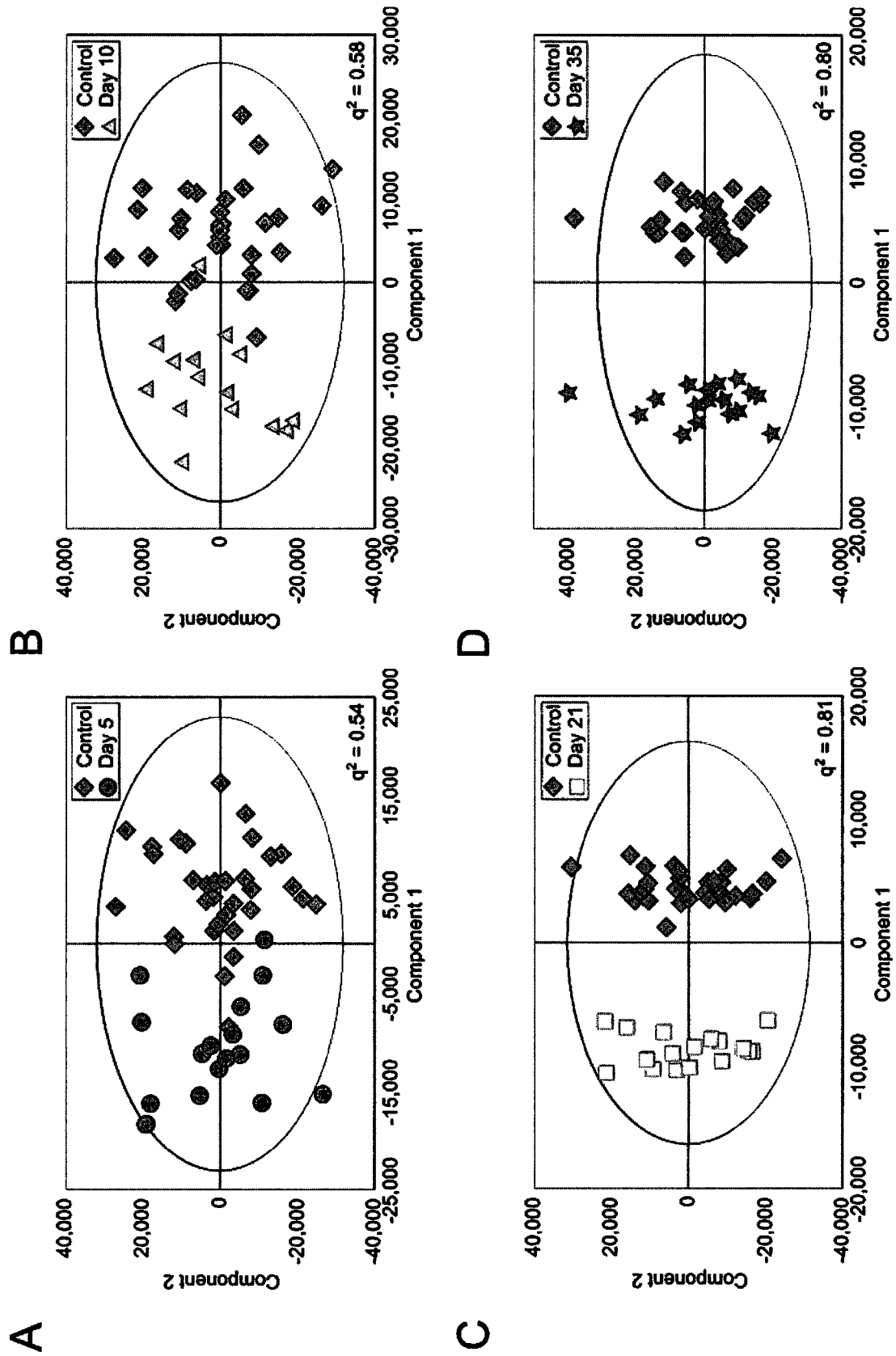
FIG. 2 shows OPLS-DA scores scatter plots for models constructed to separate urine samples from animals in control cohorts from animals at day 5 (A), 10 (B), 21 (C) and 35 (D) after intracerebral injection of 4T1-GFP cells.

Four Orthogonal Partial Least Squares Discriminant Analysis (OPLS-DA) models were constructed separating NMR spectra of urine samples obtained from mice 5, 10, 21 or 35 days after 4T1-GFP cell injection from their respective control cohorts. The study design, including control groupings, is shown in FIG. 1. All four models were significantly predictive with models from later time points being stronger than those from earlier time points (FIG. 2). For days 5, 10, 21 and 35, $q^2$ values were 0.54, 0.58, 0.81 and 0.80, respectively whilst CV-ANOVA p-values were $3.0 \times 10^{-7}$, $6.1 \times 10^{-6}$, $6.7 \times 10^{-8}$ and $1.5 \times 10^{-8}$, respectively; $q^2$ values >0.4 are considered biologically significant.

Figure 3:
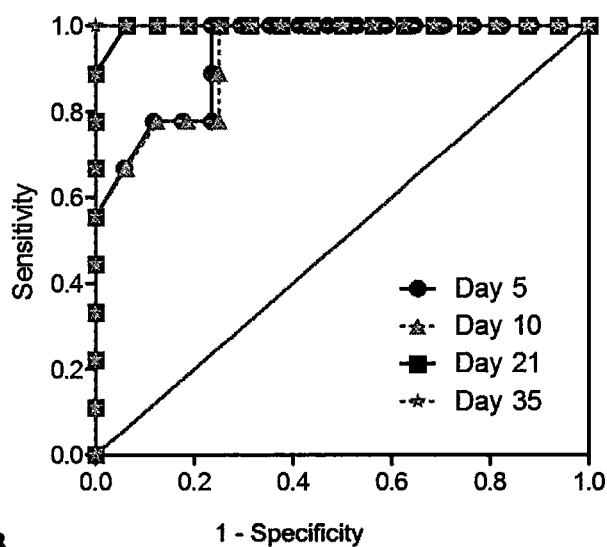
FIG. 3 shows prediction results from OPLS-DA models separating animals at different time points after intracerebral injection of 4T1-GFP cells represented as (A) ROC curves and (B to E) 2×2 contingency tables for days 5, 10, 21 and 35.

To validate the predictive ability of each model, the subset of samples withheld from the modelling procedure was used as a testing set (FIG. 1). In each case, the unknown samples were assigned to either control or 4T1-GFP injected groups by the relevant model, and contingency tables and ROC curves constructed (FIG. 3). Each model was highly sensitive and specific in separating the disease and control groups; sensitivity and specificity was 0.78 and 0.76 at day 5, 0.78 and 0.75 at day 10, 0.89 and 1.00 at day 21, and 1.00 and 1.00 at day 35.

Figure 4:
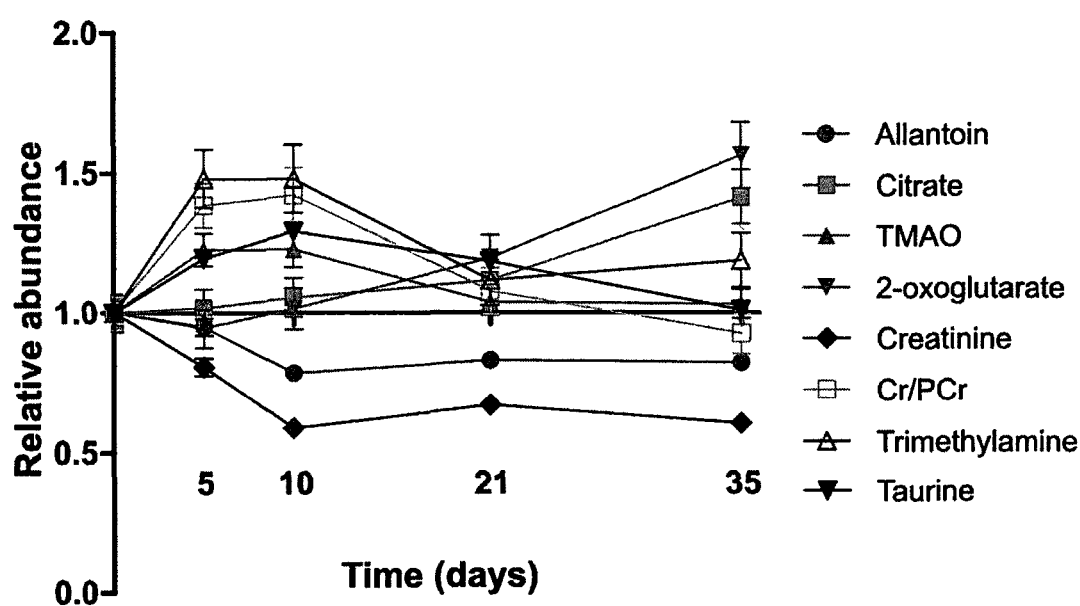
FIG. 4 shows metabolite concentration changes throughout the 4T1-GFP metastasis timecourse. Abundances are shown relative to that found in each control population. Data points are shown as mean±SEM. n=17 for each timepoint.
Figure 7:
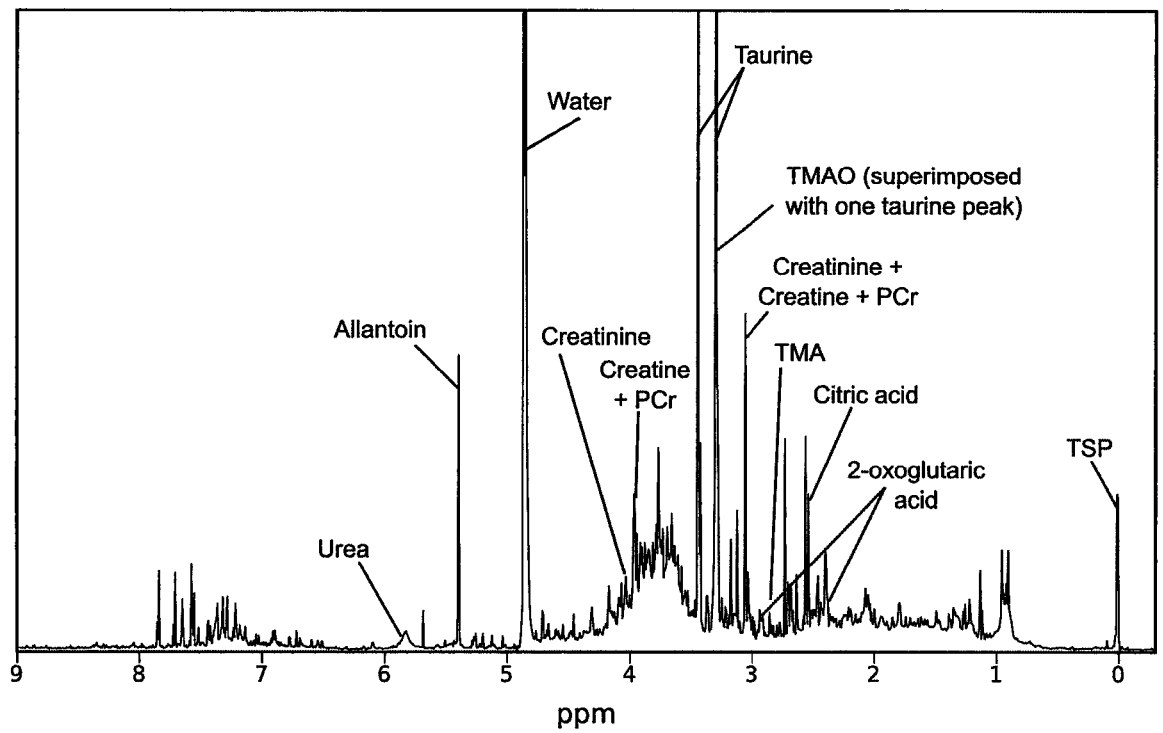
FIG. 7 shows example urine NMR spectrum with peaks of interest annotated. PCr=Phosphocreatine. TSP=3-trimethylsilyl-1-[2,2,3,3,-$^2$H$_4$] propionate.

Eight metabolites were identified from the variable importance in projection (VIP) plots as contributing the most to the separation of some or all of the models. These metabolites were allantoin ($\delta$=5.38-5.39), citrate ($\delta$=2.52-2.53), trimethylamine (TMA, $\delta$=2.89-2.90), trimethylamine-N-oxide (TMAO, $\delta$=3.27-3.28), 2-oxoglutarate ($\delta$=2.43-2.45), creatinine ($\delta$=4.06-4.07 and/or $\delta$=3.03-3.04), taurine ($\delta$=3.27-3.44) and creatine+phosphocreatine (Cr+PCr, indistinguishable by $^1$H NMR at this pH; $\delta$=3.93-3.94). Where metabolite peaks span a number of buckets, only the most important buckets are listed. The abundance of each of these metabolites relative to the control group is shown in FIG. 4 and a representative NMR spectrum is given in FIG. 7.

TMA, TMAO, Cr+PCr and taurine were all more abundant in the early stages of tumour development with their importance for model separation decreasing by day 21. Creatinine and allantoin both decreased in abundance as tumours developed from day 0 to day 10 (creatinine p<0.001 by day 5, allantoin p<0.001 by day 10). From day 10 to day 35, their relative abundance remained unchanged at around 63% of control for creatinine and 82% of control for allantoin. Citrate and 2-oxoglutarate both underwent no change in the early time points (days 5 and 10), but then increased in abundance continuously throughout the remainder of the timecourse to reach significance by day 35 (p<0.001).

Differing CNS and Systemic Tumour Burdens

Two OPLS-DA models were built to compare animals injected with 4T1-GFP cells via either the intravenous or intracardiac route with their respective control cohorts 10 days after tumour induction.

Figure 5:
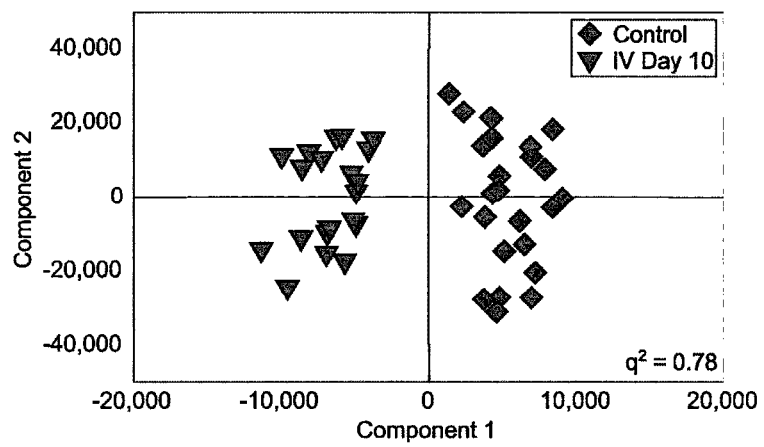
FIG. 5 shows OPLS-DA scores scatter plots for models constructed to separate urine samples from animals in control cohorts from animals at day 10 after injection of 4T1-GFP tumour cells either (A) intravenously or (B) intracardially. (C) Relative abundances of key metabolites in 4T1-GFP brain metastasis models with tumour induction by differing routes. Each metabolite's abundance is shown relative to each group's control cohort abundance at day 10 after injection. Intracerebral injections are shown with black bars (n=50), intracardiac injections are shown with grey bars (n=44) and intravenous injections are shown with open bars (n=44). Data are means±SEM.
Figure 5:
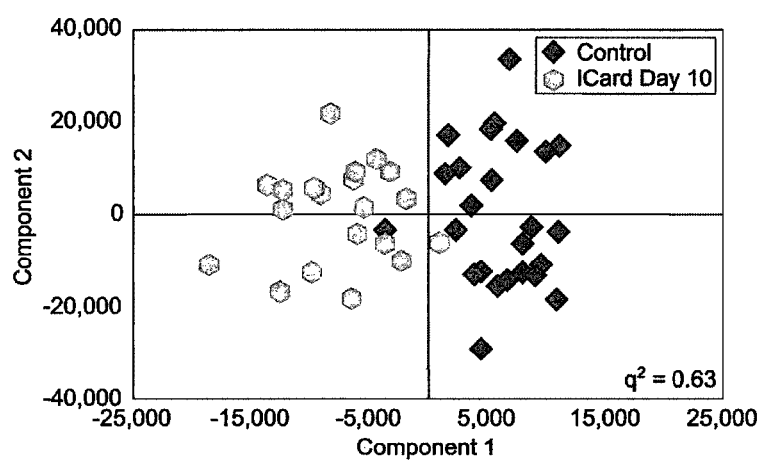
Figure 5:
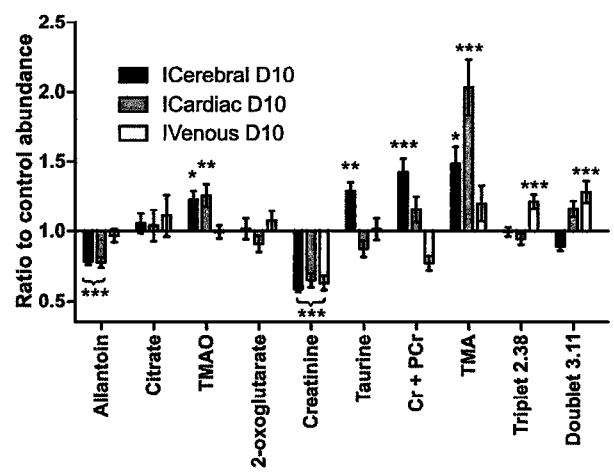

Both models were significantly predictive with $q^2$ values of 0.78 and 0.63 for intravenous and intracardiac routes, respectively, and CV-ANOVA p-values of $4.7 \times 10^{-8}$ and $8.8 \times 10^{-4}$, respectively (FIGS. 5A and B). No overt clinical signs were evident and no significant changes in weight were observed in any group by sacrifice at day 10.

Since the intracardiac and intravenous models used animals at day 10 after tumour induction, these two models were then compared to the intracerebral model generated from animals at the same timepoint. All three models were significantly predictive, so the metabolite variations underpinning each model's separations were compared to identify any commonalities. Initially, only the seven metabolites identified as contributing most strongly to the timecourse of tumour progression in the intracerebral model were considered. The abundance of each metabolite relative to the control cohort in each model is presented in FIG. 5C.

Creatinine abundance was significantly decreased to almost the same extent in models induced by all three routes of induction (0.59, 0.65 and 0.63× control in the intracerebral, intracardiac and intravenous models respectively; p<0.001). Allantoin, TMA and TMAO were all unchanged in the intravenous model but in the intracardiac model allantoin was decreased (0.79× control, p<0.001) whilst TMA and TMAO were increased (2.03 and 1.23× control; p<0.001 and p<0.01 respectively), in line with the changes seen in the intracerebral model. Creatine+phosphocreatine was only significantly increased in the intracerebral model (1.42× control; p<0.001). Neither the increase in Cr+PCr in the intracardiac model (1.16× control), nor the decrease in the intravenous model (0.77× control) reached significance (p>0.05). Despite being increased in the intracerebral model (1.29× control; p<0.01), taurine was not changed significantly in the intracardiac or intravenous models (p>0.05). No change in abundance of either citrate or 2-oxoglutarate was observed in any model at day 10; these two metabolites only change significantly at later timepoints in the intracerebral timecourse (FIG. 4).

In addition to changes in these metabolites, two other metabolites were also identified as contributing substantially to the separations in the alternative injection route models. An unidentified triplet centred at δ=2.38 and an unidentified doublet at δ=3.11 were both increased in the intravenous model (1.21 and 1.28× control respectively; p<0.001), but showed no significant changes in either the intracerebral or intracardiac models.

Example 2

In order to validate the proposed biofluid metabolomics approach for the early detection of brain metastasis, two further experimental models were considered: (i) metastatic human breast carcinoma cells (MDA-231-BR-GFP) injected intracerebrally in SCID mice; and (ii) metastatic mouse melanoma cells (B16F10) injected intracerebrally in syngeneic C57BL/6 mice.

Methods

For each model, urine samples were collected from animals 10 days after intracerebral injection with tumour cells (MDA-231-BR-GFP, n=5; B16F10, n=6) or PBS-vehicle alone (n=6 and n=5, respectively). Samples from naïve animals (n=5 for each cell line) were also collected. Samples from naïve and PBS-injected animals were combined into a single control cohort, as for the 4T1-GFP models (see Example 1). In each case, OPLS-DA models were constructed and q2 values determined. Integral regions contributing strongly to each separation were identified.

Results

Figure 8:
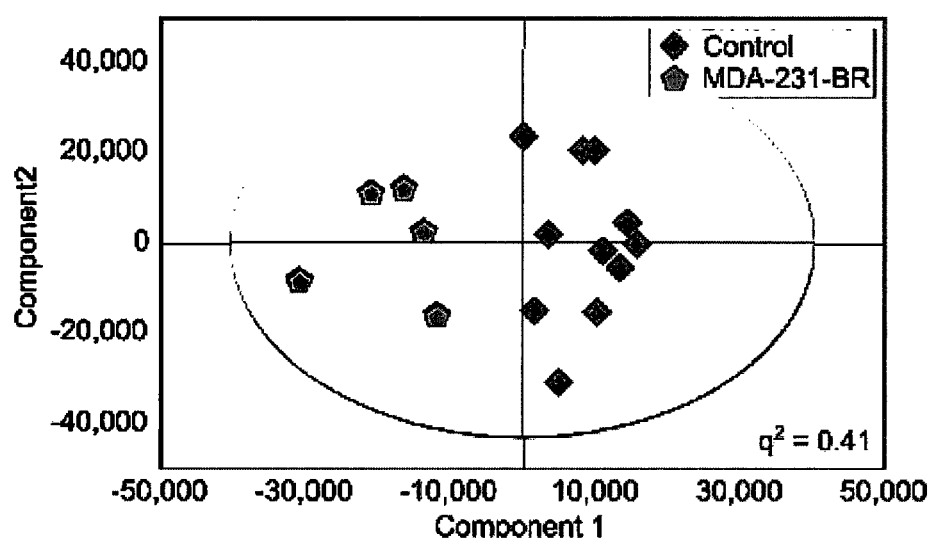
FIG. 8 shows an OPLS-DA plot of MDA-231-BR-GFP cell cohort vs. control in SCID mice.
Figure 9:
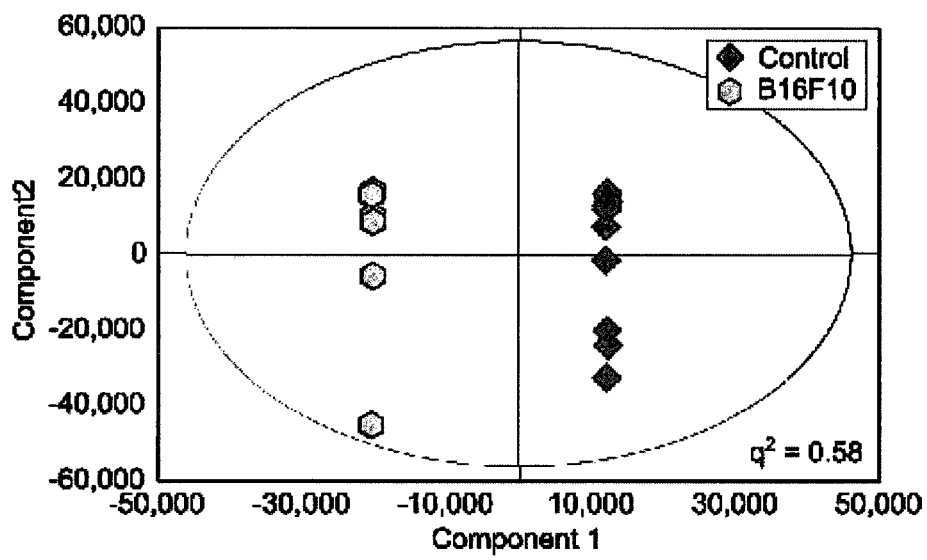
FIG. 9 shows an OPLS-DA plot of B16F10 cell cohort vs. control in C57/BL6 mice.

In each case, models with q2 values greater than the defined significance of 0.4 were produced (FIGS. 8 and 9), demonstrating that there is a predictive element to each model irrespective of tumour cell origin.

It was further considered whether the major contributing metabolite changes were common between all models, or whether individual signatures were dependent on primary tumour type. A single common metabolite signature for all brain metastases would simplify clinical implementation, but the present inventors propose that this is not an essential requirement since patients to be screened for occult metastases would be clinically stratified by primary tumour type. Thus, if necessary, primary tumour type specific models could be used.

Interestingly, the creatinine/creatine-phosphocreatine resonances featured most strongly in both of the breast carcinoma metastasis models (4T1-GFP/BALB/c and MDA-231-BR-GFP/SCID), suggesting that these peaks would be prominent in a clinically translatable model for breast cancer brain metastasis.

Example 3

In order to validate the repeatability of the intracerebrally injected 4T1-GFP-based models, a small set of animals was used to replicate the models. This second cohort of animals, hereafter referred to as Cohort B, was prepared by an independent researcher (AMD) and is thus distinct from the cohort used for the main study, hereafter referred to as Cohort A.

Methods

Cohort B included urine samples from female BALB/c mice collected 10 days after intracerebral injection of either 4T1-GFP cells (n=6) or PBS vehicle alone (n=5), as well as samples from age-matched naïve mice (n=5). The samples from the PBS-injected animals and the naïve animals were combined into a single control cohort, as described in the main text (n=10). Cohort B is independent to cohort A in four important ways: (i) the independent researcher performed all scientific steps including cell culture, animal handling, solution preparation and sample analysis; (ii) cohorts A and B were temporally separated by >6 months; (iii) separate batches of animals were used; and (iv) urine NMR spectra were acquired on different days in different batches of buffer. After data acquisition, an OPLS-DA model was built using the Cohort B NMR data. To determine whether the integral regions identified as the primary drivers in models from Cohort A could generate similarly significant models from Cohort B, only the integral regions that contributed the most to the Cohort A separations were used to build the Cohort B model (VIP>2.0; n=41).

Results

Figure 10:
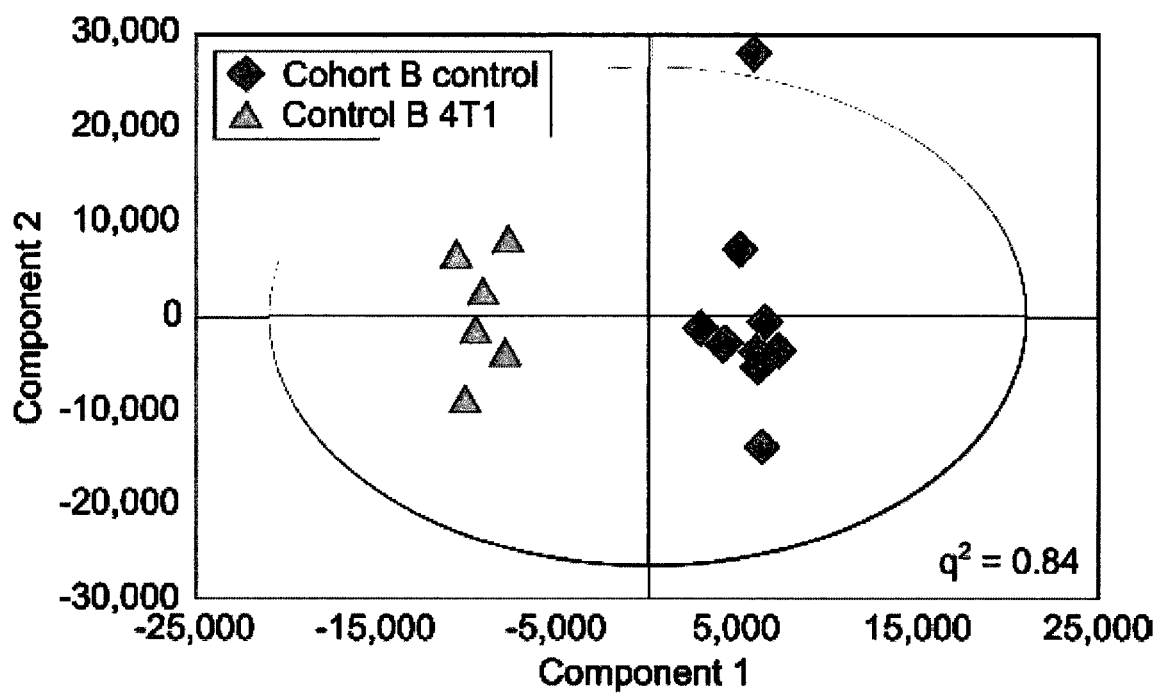
FIG. 10 shows cohort B 4T1-GFP intracerebral OPLS-DA model built using important Cohort A buckets.

The Cohort B model was significantly predictive with a q2 greater than the defined significance of 0.4 (q2=0.84; FIG. 10).

Conclusion

The Cohort B model generated in this validation study is very strongly predictive. Since Cohort B is a completely independent set of animals to Cohort A, these data demonstrate the reproducibility and robustness of the separation, and confirm that the findings are not a chance occurrence from a single batch of animals or the result of systematic bias on the part of a single operator.

Owing to careful experimental design of the control cohorts, it seems clear that the observed separations between metastasis-bearing and control animals are independent of any urinary changes induced by the intracerebral injection itself, aging or hormonal cycles across the timecourse. The ROC analysis and prediction results further show that the urinary metabolic profile, as determined by $^1$H NMR, is sufficient to sensitively and specifically distinguish animals with tumours from animals without as early as five days after tumour cell injection.

The metabolite changes present in the urine during the timecourse can be broadly divided into three groups: (i) those metabolites that didn't change significantly in the initial stages of tumour growth, bit which changed progressively across the timecourse (citrate and 2-oxoglutarate); (ii) those metabolites that were stably altered throughout the timecourse (creatinine and allantoin) and (iii) those metabolites that changed at earlier time points, but later returned to baseline values (TMAO, TMA, Cr+PCr and taurine). A combination of these changes is likely to be more indicative of the stage of a tumour than any single metabolite alone.

Figure 6:
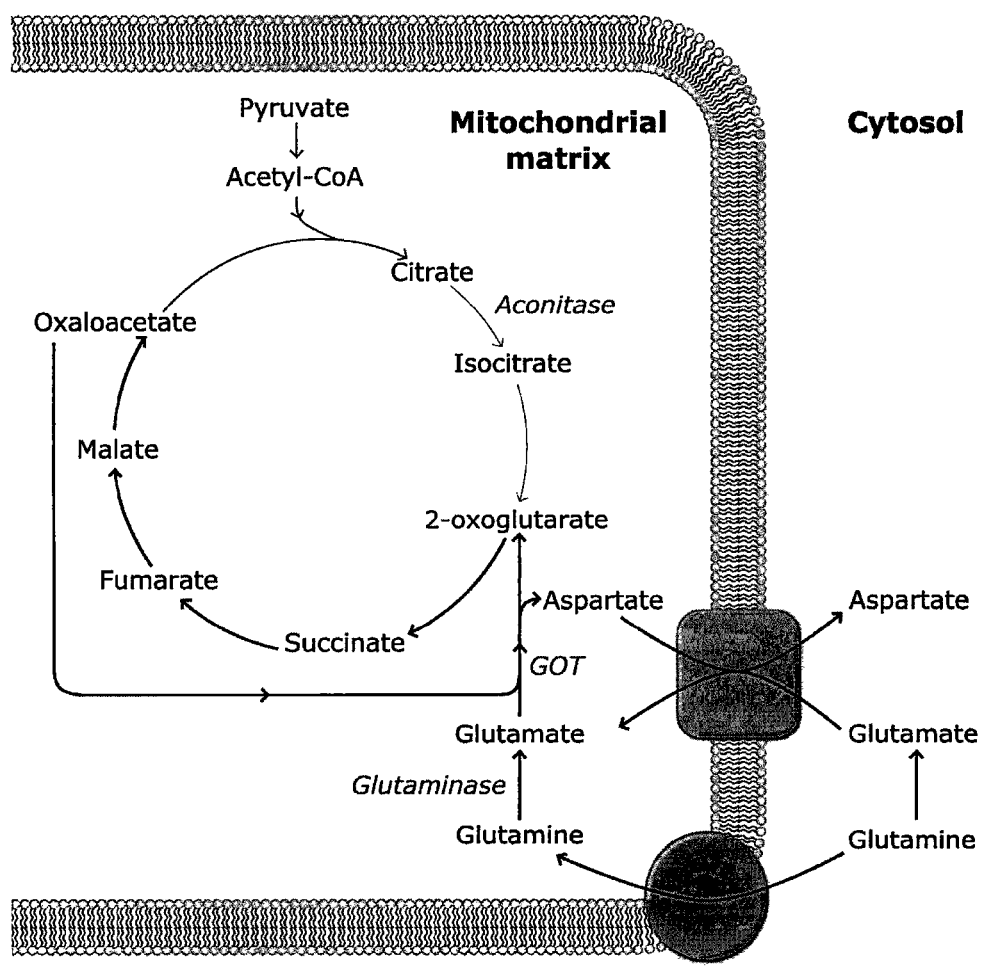
FIG. 6 shows proposed mechanism for increased citrate and 2-oxoglutarate. Pathways with increased activity in cancer are shown in bold and pathways with decreased activity are shown in feint. Enzyme names are shown in italicised text. GOT: glutamate oxaloacetate transaminase.

At first consideration, metabolites whose change increases in magnitude as tumours grow would appear to offer the best diagnostic marker for disease. In this case, citrate and 2-oxoglutarate are both intermediates in the ticarboxylic acid (TCA) cycle. Normal metabolic flux in healthy cells converts citrate to 2-oxoglutarate after the reversible isomerisation of citrate to isocitrate by the enzyme aconitase (FIG. 6). However, not all carbon enters the TCA cycle via glycolysis and this is particularly true in cancer cells where glutaminolysis is a key energy source and anaplerotic reaction, with higher flux than non-tumour cells (Kim et al. 2014, Yang et al. 2014, Goto et al. 2014). Glutamine enters the TCA cycle after conversion to glutamate by glutaminase and subsequent conversion to 2-oxoglutarate by glutamate oxaloacetate transaminase. High activity of glutaminase is associated with increased proliferation of breast cancer cells (Qie et al. 2014). Furthermore, the enzyme aconitase is often inhibited in tumour cells owing to the high abundance of reactive oxygen species (ROS) in these cells (Kim et al. 2001). As a result, 2-oxoglutarate and citrate concentrations are likely to be elevated owing to enhanced glutaminolysis and aconitase inhibition, respectively (FIG. 6). Since the increase in flux through these reactions is proportional to the mass of tumour cells, it is logical that these abundances increases as the tumours grow.

Allanotin is the end product of purine catabolism in mice. In higher primates, including humans, the pathway for synthesis of allantoin is absent so the breakdown of purines stops at uric acid with allantoin being formed in only small quantities by the non-enzymatic oxidation of uric acid (Il'yasova et al. 2012). Since tumour cells are highly proliferative, they have a high demand for purines for synthesis of new DNA. As such, it is possible that the decreased allantoin excretion observed is simply a function of increased demand for purines and a greater need to metabolically salvage purine breakdown products.

The major source of TMA and TMAO is dietary choline which is converted to TMA by the action of gut flora before being taken into circulation and oxidised to TMAO, likely by one of a number of members of the flavin monooxygenase family e.g. FMO3 (Zeisel et al. 1989, Bennett et al. 2013). TMA can then be re-formed by non-enzymatic degradation of TMAO. Since TMA and TMAO are closely metabolically linked, it is not surprising that their abundance profiles are broadly similar to each other. The more surprising aspect is that their profile shows a dramatic increase at very early time points before returning to baseline values at later time points. Since the diet of the animals remains the same and some animals in the control group underwent surgery, the remaining possibility is that the injected cells contained either one or both metabolites. A proton NMR spectrum obtained from a perchloric acid extract of 4T1 cells shows a significant quantity of TMAO but no TMA (data not shown). Thus it's possible that after injection a fraction of the cells do not establish in the host animal and die, releasing their metabolites. This release would include TMAO which would be cleared to the urine and, once away from the activity of FMO3, would degrade to the TMA also found in the urine. Similarly, a peak at the same position as Cr+PCr is present in the 4T1 cell extract and this would explain the unusual profile after injection.

Currently, it is possible to determine the presence of systemic metastases by either biopsy (Shields et al. 2001) or the use of specific blood markers (Weigelt et al. 2005), but the same is not true for brain metastases. The ability to detect intracerebrally injected 4T1-GFP cells at an early timepoint suggested that it may be possible to identify a set of metabolites that were specific to brain metastases, even in the presence of systemic metastases. The 4T1-GFP mouse mammary carcinoma cell line (Aslakson and Miller 1992) has been widely used as a model of metastasis. By varying the injection route, it is possible to bias the sites of resulting metastases. For example, intravenous tumour cell injections give rise to metastatic nodules primarily in the lungs, as this is the first capillary bed encountered. Alternatively, intracardiac injections put tumour cells directly into the arterial circulation which gives rise to metastases in a wider range of locations including brain, bone and adrenal glands (Saxena and Christofori 2013). Thus, by comparing commonalities between intracardiac injection and direct injection of cells into the brain, and differences from intravenous cell injection, it may be possible to identify a fingerprint for brain metastasis specifically.

The pattern of key metabolite abundance changes for the differing routes of 4T1-GFP cell injection indicates that systemic and CNS metastases may give rise to different urinary metabolic profiles, which may be super-imposable where metastases exist in both locations. For example, the decrease in allantoin observed at the day 10 time point for both the intracerebral and intracardiac injections is of particular note, since it remained changed significantly in abundance in the intravenous model. At the same time the patterns observed for creatinine, Cr+PCr and the unidentified doublet at 3.12 ppm are of interest in that the intracerebral and intravenous models appear to show opposite responses in these metabolites, whilst the intracardiac model lies between those two extremes. This arrangement may reflect a combination of systemic and intracerebral metastatic phenotypes in the intracardiac model.

Taken together, these observations suggest that the decreases in allantoin and creatinine coupled with the increases in TMAO and Cr+PCr may provide a reliable signature for metastasis within the brain specifically.

Throughout all the models investigated the ratio of Cr+PCr to allantoin is the single most likely urine metabolic marker for the presence of brain metastases, above and beyond the presence of any systemic metastases. However, allantoin is not a metabolite excreted by higher primates as the pathway for conversion of uric acid to allantoin is absent. This means that the end product of purine metabolism in humans is uric acid, a compound not visible on $^1$H NMR spectroscopy (Wevers et al. 1999), but for which cheap and quick biochemical assays exist.

One aspect of clinical care where this technique could prove useful is screening patients at a known high risk of brain metastases. Urine samples are easy and cheap to collect and the NMR analysis itself is inexpensive. A series of samples could be taken routinely from patients as they come in for their standard follow up clinics. These would be analysed and could be plotted in a dynamic fashion, giving an overview of patient progression over time. Appropriate cut-off values could be determined to allow physicians to classify patients as potentially having clinically occult brain metastases.

REFERENCES

Aslakson, C. J., and F. R. Miller. 1992. Selective events in the metastatic process defined by analysis of the sequential dissemination of subpopulations of a mouse mammary tumor. Cancer Res 52:1399-1405.

Bao, Q., J. Feng, L. Chen, F. Chen, Z. Liu, B. Jiang, and C. Liu. 2013. A robust automatic phase correction method for signal dense spectra. J Magn Reson 234:82-89.

Beckonert, O., H. C. Keun, T. M. D. Ebbels, J. Bundy, E. Holmes, J. C. Lindon, and J. K. Nicholson. 2007. Metabolic profiling, metabolomic and metabonomic procedures for NMR spectroscopy of urine, plasma, serum and tissue extracts. Nat Protoc 2:2692-2703.

Beek, J. D. van. 2007. matNMR: a flexible toolbox for processing, analyzing and visualizing magnetic resonance data in Matlab. J Magn Reson 187:19-26.

Bennett, B. J., T. Q. de Aguiar Vallim, Z. Wang, D. M. Shih, Y. Meng, J. Gregory, H. Allayee, R. Lee, M. Graham, R. Crooke, P. A. Edwards, S. L. Hazen, and A. J. Lusis. 2013. Trimethylamine-N-oxide, a metabolite associated with atherosclerosis, exhibits complex genetic and dietary regulation. Cell Metab 17:49-60.

Davis, V. W., D. E. Schiller, D. Eurich, and M. B. Sawyer. 2012. Urinary metabolomic signature of esophageal cancer and Barrett's esophagus. World J Surg Oncol 10:271.

Fan, T. W.-M. 1996. Metabolite profiling by one- and two-dimensional NMR analysis of complex mixtures. Progress in Nuclear Magnetic Resonance Spectroscopy 28:161-219.

Goto, M., H. Miwa, M. Shikami, N. Tsunekawa-Imai, K. Suganuma, S. Mizuno, M. Takahashi, M. Mizutani, I. Hanamura, and M. Nitta. 2014. Importance of glutamine metabolism in leukemia cells by energy production through TCA cycle and by redox homeostasis. Cancer Invest 32:241-247.

Graesslin, O., B. S. Abdulkarim, C. Coutant, F. Huguet, Z. Gabos, L. Hsu, O. Marpeau, S. Uzan, L. Pusztai, E. A. Strom, G. N. Hortobagyi, R. Rouzier, and N. K. Ibrahim. 2010. Nomogram to predict subsequent brain metastasis in patients with metastatic breast cancer. J Clin Oncol 28:2032-2037.

Gronwald, W., M. S. Klein, R. Zeltner, B.-D. Schulze, S. W. Reinhold, M. Deutschmann, A.-K. Immervoll, C. A. Böger, B. Banas, K.-U. Eckardt, and P. J. Oefner. 2011. Detection of autosomal dominant polycystic kidney disease by NMR spectroscopic fingerprinting of urine. Kidney Int 79:1244-1253.

Il'yasova, D., P. Scarbrough, and I. Spasojevic. 2012. Urinary biomarkers of oxidative status. Clin Chim Acta 413:1446-1453.

Kim, K. H., A. M. Rodriguez, P. M. Carrico, and J. A. Melendez. 2001. Potential mechanisms for the inhibition of tumor cell growth by manganese superoxide dismutase. Antioxid Redox Signal 3:361-373.

Kim, M.-J., D.-H. Kim, W.-H. Jung, and J.-S. Koo. 2014. Expression of metabolism-related proteins in triple-negative breast cancer. Int J Clin Exp Pathol 7:301-312.

Qie, S., C. Chu, W. Li, C. Wang, and N. Sang. 2014. ErbB2 activation upregulates glutaminase 1 expression which promotes breast cancer cell proliferation. J Cell Biochem 115:498-509.

Saxena, M., and G. Christofori. 2013. Rebuilding cancer metastasis in the mouse. Mol Oncol 7:283-296.

Serres, S., M. S. Soto, A. Hamilton, M. A. McAteer, W. S. Carbonell, M. D. Robson, O. Ansorge, A. Khrapitchev, C. Bristow, L. Balathasan, T. Weissensteiner, D. C. Anthony, R. P. Choudhury, R. J. Muschel, and N. R. Sibson. 2012. Molecular MRI enables early and sensitive detection of brain metastases. Proc Natl Acad Sci USA 109:6674-6679.

Shields, J. A., C. L. Shields, H. K. Brotman, C. Carvalho, N. Perez, and R. Jr Eagle. 2001. Cancer metastatic to the orbit: the 2000 Robert M. Curts Lecture. Ophthal Plast Reconstr Surg 17:346-354.

Skov, T., F. van den Berg, G. Tomasi, and R. Bro. 2006. Automated alignment of chromatographic data. Journal of Chemometrics 20:487-497.

Waterman, C. L., R. A. Currie, L. A. Cottrell, J. Dow, J. Wright, C. J. Waterfield, and J. L. Griffin. 2010. An integrated functional genomic study of acute phenobarbital exposure in the rat. BMC Genomics 11:9.

Weigelt, B., J. L. Peterse, and L. J. van t Veer. 2005. Breast cancer metastasis: markers and models. Nat Rev Cancer 5:591-602.

Wevers, R. A., U. F. Engelke, S. H. Moolenaar, C. Bräutigam, J. G. de Jong, R. Duran, R. A. de Abreu, and A. H. van Gennip. 1999. 1H-NMR spectroscopy of body fluids: inborn errors of purine and pyrimidine metabolism. Clin Chem 45:539-548.

Wishart, D. S., T. Jewison, A. C. Guo, M. Wilson, C. Knox, Y. Liu, Y. Djoumbou, R. Mandal, F. Aziat, E. Dong, S. Bouatra, I. Sinelnikov, D. Arndt, J. Xia, P. Liu, F. Yallou, T. Bjorndahl, R. Perez-Pineiro, R. Eisner, F. Allen, V. Neveu, R. Greiner, and A. Scalbert. 2013. HMDB 3.0—The Human Metabolome Database in 2013. Nucleic Acids Res 41:D801-D807.

Xie, G. X., T. L. Chen, Y. P. Qiu, P. Shi, X. J. Zheng, M. M. Su, A. H. Zhao, Z. T. Zhou, and W. Jia. 2012. Urine metabolite profiling offers potential early diagnosis of oral cancer. Metabolomics 8:220-231.

Yang, L., T. Moss, L. S. Mangala, J. Marini, H. Zhao, S. Wahlig, G. Armaiz-Pena, D. Jiang, A. Achreja, J. Win, R. Roopaimoole, C. Rodriguez-Aguayo, I. Mercado-Uribe, G. Lopez-Berestein, J. Liu, T. Tsukamoto, A. K. Sood, P. T. Ram, and D. Nagrath. 2014. Metabolic shifts toward glutamine regulate tumor growth, invasion and bioenergetics in ovarian cancer. Mol Syst Biol 10:728.

Zeisel, S. H., K. A. daCosta, M. Youssef, and S. Hensey. 1989. Conversion of dietary choline to trimethylamine and dimethylamine in rats: dose-response relationship. J Nutr 119:800-804.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. An in vitro method for identifying an elevated concentration of at least one metabolite comprising trimethylamine (TMA), triethylamine-N-oxide (TMAO), taurine, creatine, or phosphocreatine or a reduced concentration of at least one metabolite comprising uric acid or creatinine, combinations thereof in a biofluid sample obtained from a human test subject with a possible brain tumor, the method comprising:

a) detecting the concentration of at least two of TMA, TMAO, taurine, creatine, phosphocreatine, uric acid and creatinine by nuclear magnetic resonance (NMR) spectroscopy, mass spectroscopy, HPLC-UV, infrared spectroscopy, or a biochemical assay in the biofluid sample, and b) comparing the concentration of the at least two of TMA, TMAO, taurine, creatine, phosphocreatine, uric acid, and creatinine in the biofluid sample from the human subject with a possible brain tumor to a control concentration of TMA, TMAO, taurine, creatine, phosphocreatine, uric acid, and/or creatine in at least one reference standard from at least one non-tumor bearing human subject, and c) identifying a concentration difference for each of the at least two of TMA, TMAO, taurine, creatine, phosphocreatine, uric acid and creatine in the biofluid sample relative to the at least one reference standard; wherein the concentration difference for each of the at least two of TMA, TMAO, taurine, creatine, phosphocreatine, uric acid and creatinine is: an elevated concentration when the metabolite is TMA, TMAO, taurine, creatine, or phosphocreatine, and a reduced concentration when the metabolite is uric acid or creatinine;

wherein TMA, TMAO, taurine, creatine, and/or phosphocreatine are elevated in concentration, and/or uric acid and/or creatinine are reduced in concentration when a brain tumor is present.

2. The in vitro method according to claim 1, wherein at least one metabolite is TMAO, creatine, or phosphocreatine or combinations thereof, and at least one metabolite is uric acid, or creatinine or combinations thereof.

3. The method according to claim 2, wherein the concentration of TMAO, creatine, phosphocreatine or combinations thereof detected is higher in the biofluid sample obtained from a human test subject than in the at least one reference standard obtained from a non-tumor bearing human subject, and wherein the concentration of uric acid, creatinine, or combinations thereof detected is lower in the biofluid sample obtained from a human test subject than in the at least one reference standard obtained from the non-tumor bearing human subject.

4. The method according to claim 1, wherein the concentration of the at least two metabolites is detected by one or more methods selected from the group consisting of: nuclear magnetic resonance (NMR) spectroscopy, mass spectrometry, HPLC-UV, infrared spectrometry and a biochemical assay.

5. The method according to claim 1, wherein the concentration of the at least two metabolites is detected by $^1$H NMR spectroscopy.

6. The method according to claim 1, wherein the concentration of at least 3, 4, 5, 6 or more metabolites is measured.

7. The method according to claim 1, wherein a higher concentration of TMAO, taurine, creatine, phosphocreatine, TMA or combinations thereof is detected in the biofluid sample obtained from a human test subject than in at least one reference standard obtained from a human subject with systemic metastases, and detecting a lower concentration of uric acid, an unidentified metabolite having a triplet at $\delta=2.38$, an unidentified metabolite having a doublet at $\delta=3.11$, or combinations thereof in the biofluid sample obtained from a human test subject than in the at least one reference standard obtained from a human subject with systemic metastases.

8. The method according to claim 1, wherein the biofluid sample is a urine sample, a blood sample, cerebrospinal fluid sample, combinations thereof or fractions thereof.

9. The method according to 1, further comprising recording the output of at least one step on a data-storage medium.

10. A method of treating a brain tumor in a human subject, said method comprising:
 a. obtaining the results of an in vitro method, wherein said method comprises:
   detecting a concentration of at least two metabolites comprised in a biofluid sample obtained from the human subject, wherein said at least two metabolites are TMA, TMAO, taurine, creatine, phosphocreatine, uric acid, or creatinine; and
   wherein TMA, TMAO, taurine, creatine, or phosphocreatine when detected are higher in concentration in the biofluid sample obtained from the human subject than in at least one reference standard obtained from a non-tumor bearing subject, and wherein uric acid or creatinine when detected are lower in concentration in the biofluid sample obtained from the human subject than in the at least one reference standard from the non-tumor bearing subject when the subject is determined to have a brain tumor; and
 b. administering to the human subject determined to have a brain tumor a treatment directed to the brain tumor.

11. The method according to claim 10, wherein the brain tumor is a primary or a secondary brain tumor.

* * * * *

UNITED STATES PATENT AND TRADEMARK OFFICE
CERTIFICATE OF CORRECTION

PATENT NO. : 10,859,576 B2  
APPLICATION NO. : 15/578925  
DATED : December 8, 2020  
INVENTOR(S) : N. R. Sibson et al.

Page 1 of 1

It is certified that error appears in the above-identified patent and that said Letters Patent is hereby corrected as shown below:

In the Claims

| Column | Line | |
| --- | --- | --- |
| 38 (Claim 1, Line 5) | 41 | "creatinine, combinations" should read -- creatinine, or combinations -- |
| 38 (Claim 1, Line 19) | 55 | "and/or creatine" should read -- and/or creatinine -- |
| 38 (Claim 1, Line 24) | 60 | "and creatine" should read -- and creatinine -- |
| 39 (Claim 2, Line 1) | 5 | "The in vitro method" should read -- The method -- |
| 39 (Claim 7, Line 6) | 35 | "and detecting a" should read -- and a -- |
| 40 (Claim 7, Line 9) | 3 | "thereof in" should read -- thereof is detected in -- |
| 40 (Claim 8, Line 2) | 8 | "sample, cerebrospinal" should read -- sample, a cerebrospinal -- |
| 40 (Claim 9, Line 1) | 10 | "to 1" should read -- to claim 1 -- |
| 40 (Claim 10, Line 6) | 17 and 18 | "from the human" should read -- from a human -- |

Signed and Sealed this  
Eleventh Day of May, 2021

Drew Hirshfeld  
*Performing the Functions and Duties of the*  
*Under Secretary of Commerce for Intellectual Property and*  
*Director of the United States Patent and Trademark Office*